(12) United States Patent
Saito

(10) Patent No.: US 12,171,405 B2
(45) Date of Patent: Dec. 24, 2024

(54) ENDOSCOPE

(71) Applicant: OLYMPUS CORPORATION, Tokyo (JP)

(72) Inventor: Hidetoshi Saito, Hanno (JP)

(73) Assignee: OLYMPUS CORPORATION, Tokyo (JP)

(*) Notice: Subject to any disclaimer, the term of this patent is extended or adjusted under 35 U.S.C. 154(b) by 659 days.

(21) Appl. No.: 17/386,664

(22) Filed: Jul. 28, 2021

(65) Prior Publication Data

US 2021/0353131 A1 Nov. 18, 2021

Related U.S. Application Data

(63) Continuation of application No. PCT/JP2019/004863, filed on Feb. 12, 2019.

(51) Int. Cl.
*A61B 1/00* (2006.01)
*A61B 1/005* (2006.01)

(52) U.S. Cl.
CPC .................. *A61B 1/0052* (2013.01)

(58) Field of Classification Search
CPC .......... A61B 1/0052; A61B 1/00066
See application file for complete search history.

(56) References Cited

U.S. PATENT DOCUMENTS

2008/0275303 A1 11/2008 Koitabashi
2016/0309985 A1* 10/2016 Akui ................. A61B 1/044

2017/0196435 A1 7/2017 Sato et al.
2018/0310803 A1 11/2018 Hatano et al.
2019/0014972 A1* 1/2019 Hatano ................ A61B 1/0052
2019/0014974 A1* 1/2019 Hatano .............. G02B 23/2423

FOREIGN PATENT DOCUMENTS

| EP | 1 946 694 A1 | 7/2008 |
| EP | 3 202 302 A1 | 8/2017 |
| JP | 2007-130309 A | 5/2007 |
| JP | 2015-019748 A | 2/2015 |
| JP | 2015-093052 A | 5/2015 |

(Continued)

OTHER PUBLICATIONS

International Search Report dated May 7, 2019 received in PCT/JP2019/004863.
English language abstract only of EP 3 078 318 A1.

*Primary Examiner* — Timothy J Neal
(74) *Attorney, Agent, or Firm* — Scully, Scott, Murphy & Presser, P.C.

(57) ABSTRACT

To achieve an accurate bending operation in a specific direction on a joystick-type bending lever, an endoscope includes: a bending operation mechanism including a bending lever configured to be tilted in all directions including a first direction, a second direction, a third direction, and a fourth direction corresponding to bending directions in up, down, left, and right directions, respectively, of a bending portion; a long hole provided in the bending operation mechanism; and an engagement pin provided on an operation portion and configured to engage with the long hole. The engagement pin is guided into the long hole and the bending operation mechanism is supported such that the bending operation mechanism is movable relative to the operation portion.

20 Claims, 23 Drawing Sheets

(56) References Cited

FOREIGN PATENT DOCUMENTS

| | | |
|---|---|---|
| JP | 5930255 B2 | 6/2016 |
| WO | 2007/055163 A1 | 5/2007 |
| WO | 2016/052147 A1 | 4/2016 |
| WO | 2016/199485 A1 | 12/2016 |
| WO | 2016/203818 A1 | 12/2016 |
| WO | 2017/119162 A1 | 7/2017 |
| WO | 2018/128001 A1 | 7/2018 |

\* cited by examiner

ENDOSCOPE

CROSS REFERENCE TO RELATED APPLICATION

This application is a continuation application of PCT/JP2019/004863 filed on Feb. 12, 2019, the entire contents of which are incorporated herein by this reference.

BACKGROUND OF THE INVENTION

1. Field of the Invention

The present invention relates to an endoscope having a configuration in which a bending portion performs a bending operation in conjunction with a tilting operation of a joystick-type bending lever.

2. Description of the Related Art

Heretofore, an endoscope that can be inserted into a subject has been widely used in, for example, a medical field or an industrial field so as to observe a location within a subject which cannot be easily observed, such as within a living body or within a structure.

An insertion portion of such an endoscope is provided with a bending portion to improve the insertion properties, observation properties, and the like. The bending portion is bent by a bending operation mechanism provided on an operation portion.

As a bending operation mechanism of this type, a configuration in which upper and lower bending operation knobs and left and right bending operation knobs that are arranged in a superimposed manner at side portions of the operation portion are provided as operation input portions is known.

As a bending operation mechanism particularly suitable for an endoscope including a small-diameter bending portion that does not require a large operation force for a bending operation, for example, International Publication No. WO2016/203818 discloses a configuration in which a joystick-type bending lever that can be tilted in any direction is provided as an operation input portion.

Such a joystick-type bending lever enables a bending lever tilting operation in all directions by a thumb or the like of a hand grasping the operation portion. Accordingly, the bending operation in an up-down direction and a left-right direction can be performed by a simpler bending operation than that for operation knobs.

SUMMARY OF THE INVENTION

An endoscope according to an aspect of the present invention includes: a bending operation mechanism including a lever configured to be tilted in all directions including a first direction, a second direction, a third direction, and a fourth direction to cause a bending portion provided in an insertion portion configured to be inserted into a subject to be bent in all directions including, up, down, left, and right directions, the first direction, the second direction, the third direction, and the fourth direction corresponding to the up, down, left, and right directions, respectively; an operation portion provided at a proximal end side of the insertion portion, the operation portion being provided with the bending operation mechanism and provided with a grasping portion configured to be grasped by an operator; a long hole provided in one of the bending operation mechanism and the operation portion; and an engagement pin configured to engage with the long hole, the engagement pin being provided in another of the bending operation mechanism and the operation portion. The engagement pin is guided into the long hole and the bending operation mechanism is supported such that the bending operation mechanism is movable relative to the operation portion.

Further, an endoscope according to another aspect of the present invention includes: a bending operation mechanism including a lever configured to be tilted in all directions including a first direction, a second direction, a third direction, and a fourth direction to cause a bending portion provided in an insertion portion configured to be inserted into a subject to be bent in all directions including, up, down, left, and right directions, the first direction, the second direction, the third direction, and the fourth direction corresponding to the up, down, left, and right directions, respectively; and an operation portion provided at a proximal end side of the insertion portion, the operation portion being provided with the bending operation mechanism and provided with a grasping portion configured to be grasped by an operator. The first direction, the second direction, the third direction, and the fourth direction are displaceable with respect to the operation portion when the bending operation mechanism is rotated about a rotation axis intersecting a central axis of the lever located at a neutral position.

DETAILED DESCRIPTION OF THE PREFERRED EMBODIMENTS

Figure 1:
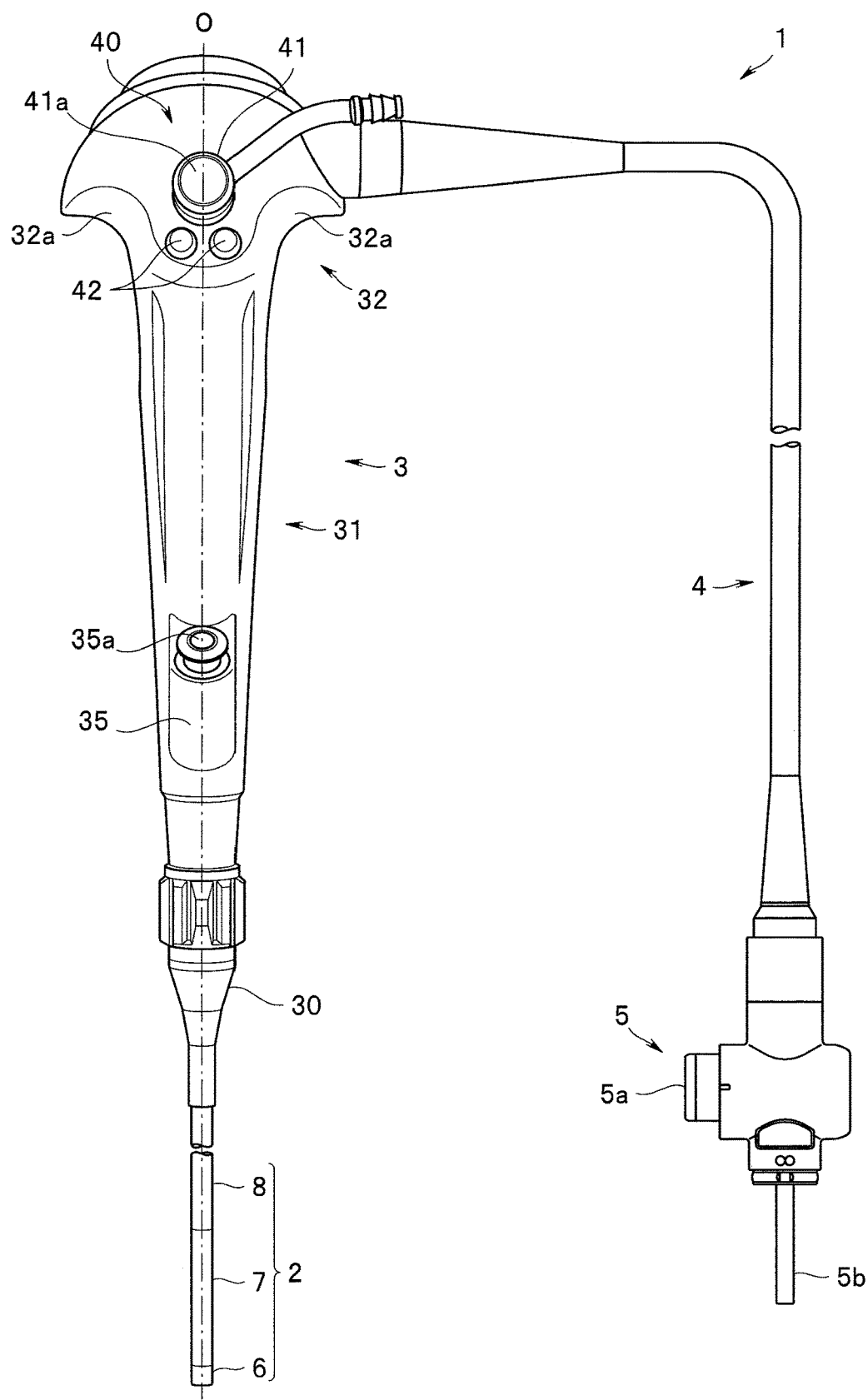
FIG. 1 is a front view illustrating an appearance of an endoscope.
Figure 2:
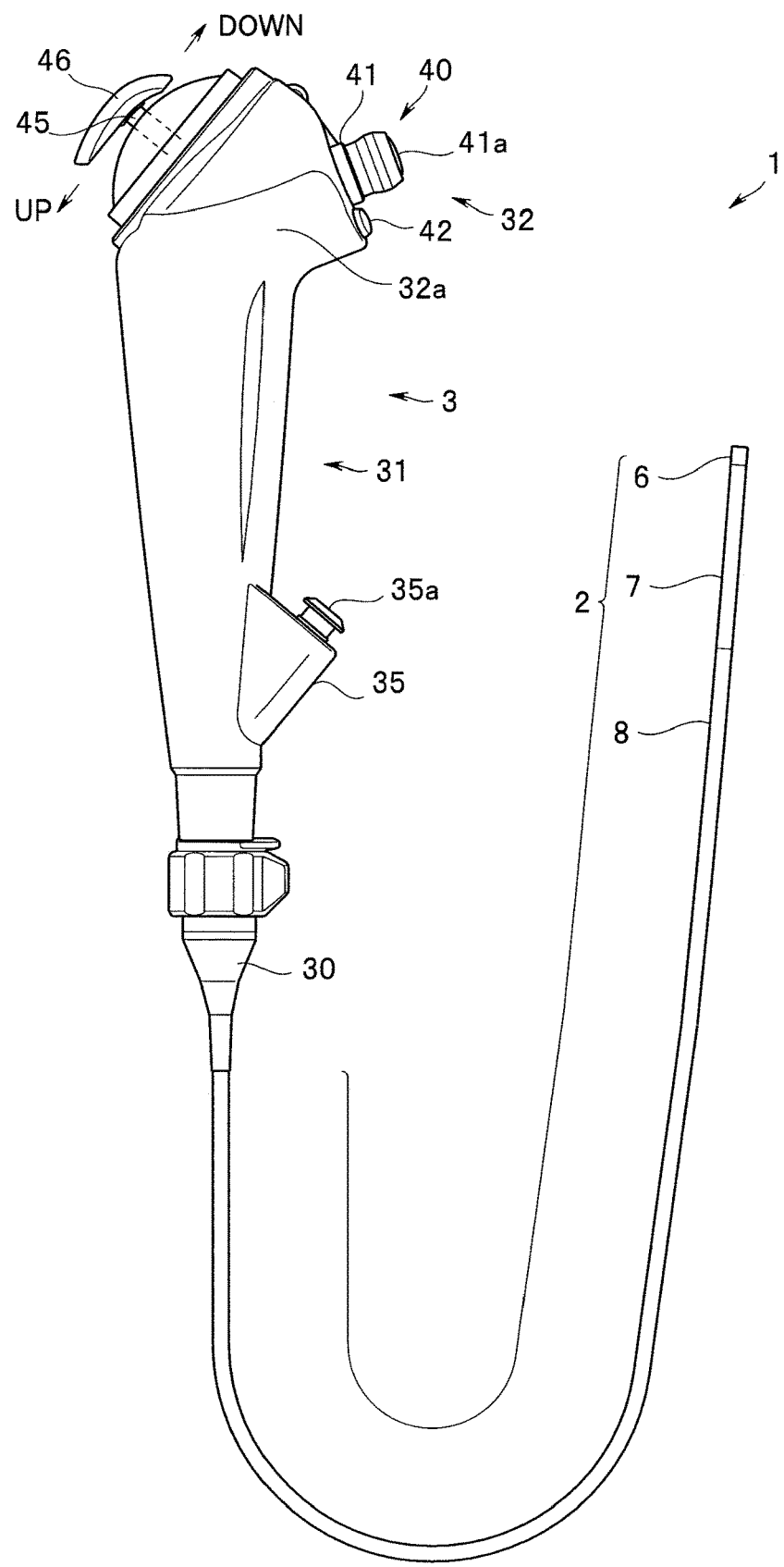
FIG. 2 is a right side view illustrating the appearance of the endoscope.

Embodiments of the present invention will be described below with reference to the drawings. FIGS. 1 to 11 relate to an embodiment of the present invention. FIG. 1 is a front view illustrating an appearance of an endoscope, and FIG. 2 is a right side view illustrating the appearance of the endoscope.

An endoscope 1 according to the present embodiment illustrated in FIGS. 1 and 2 is an electron endoscope for bronchial tube. The endoscope 1 includes an insertion portion 2 formed in an elongated shape, an operation portion 3 connected to a proximal end of the insertion portion 2, a universal cord 4 that is an endoscope cable extending from the operation portion 3, and an endoscope connector 5 disposed at a distal end of the universal cord 4.

The insertion portion 2 is configured using a tube-like member that has flexibility and has a configuration in which a distal end portion 6, a bending portion 7, and a flexible tube portion 8 are connected in order from the distal end side.

Figure 3:
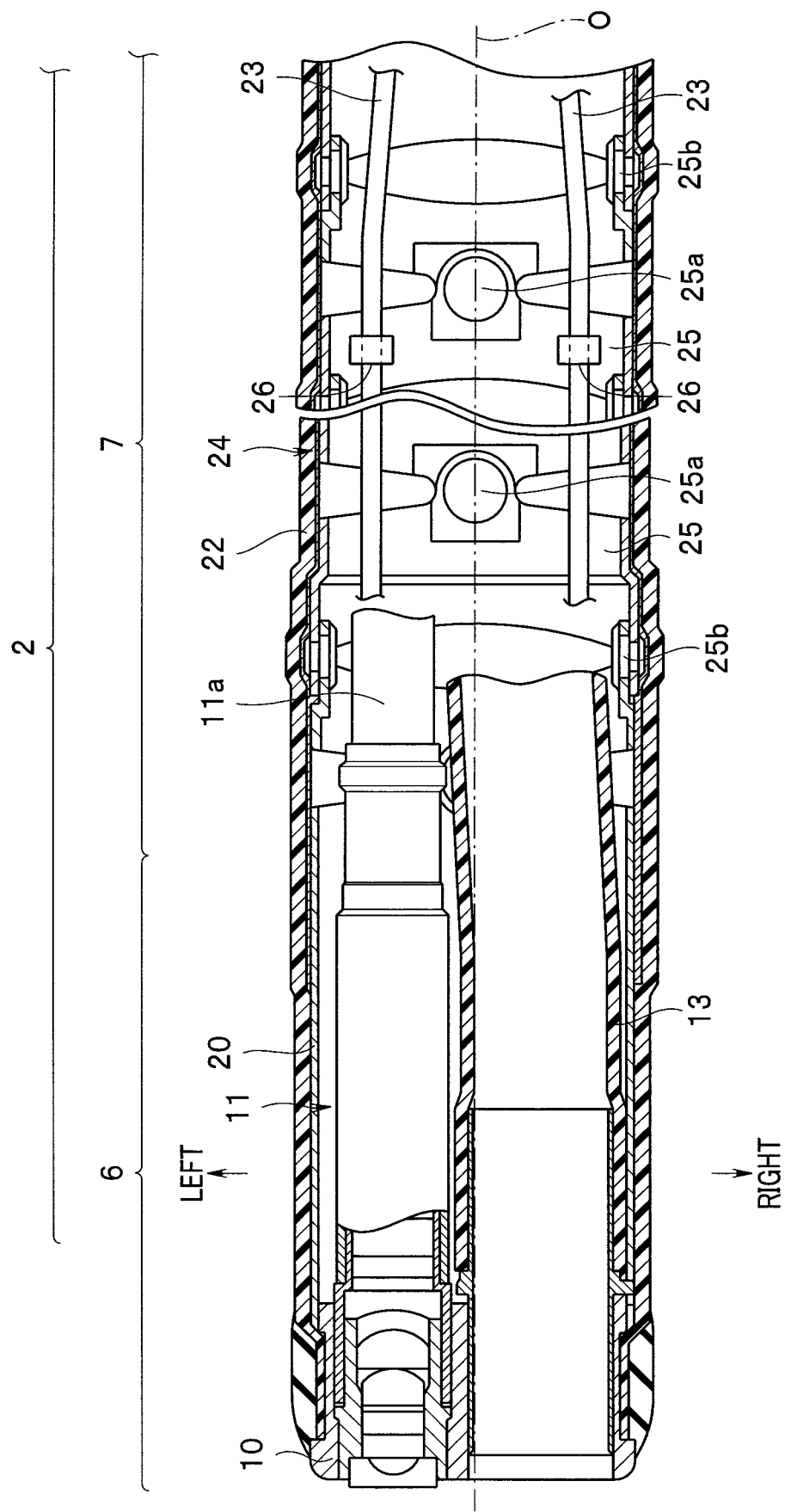
FIG. 3 is a cross-sectional view illustrating a major portion of each of a distal end portion and a bending portion.
Figure 4:
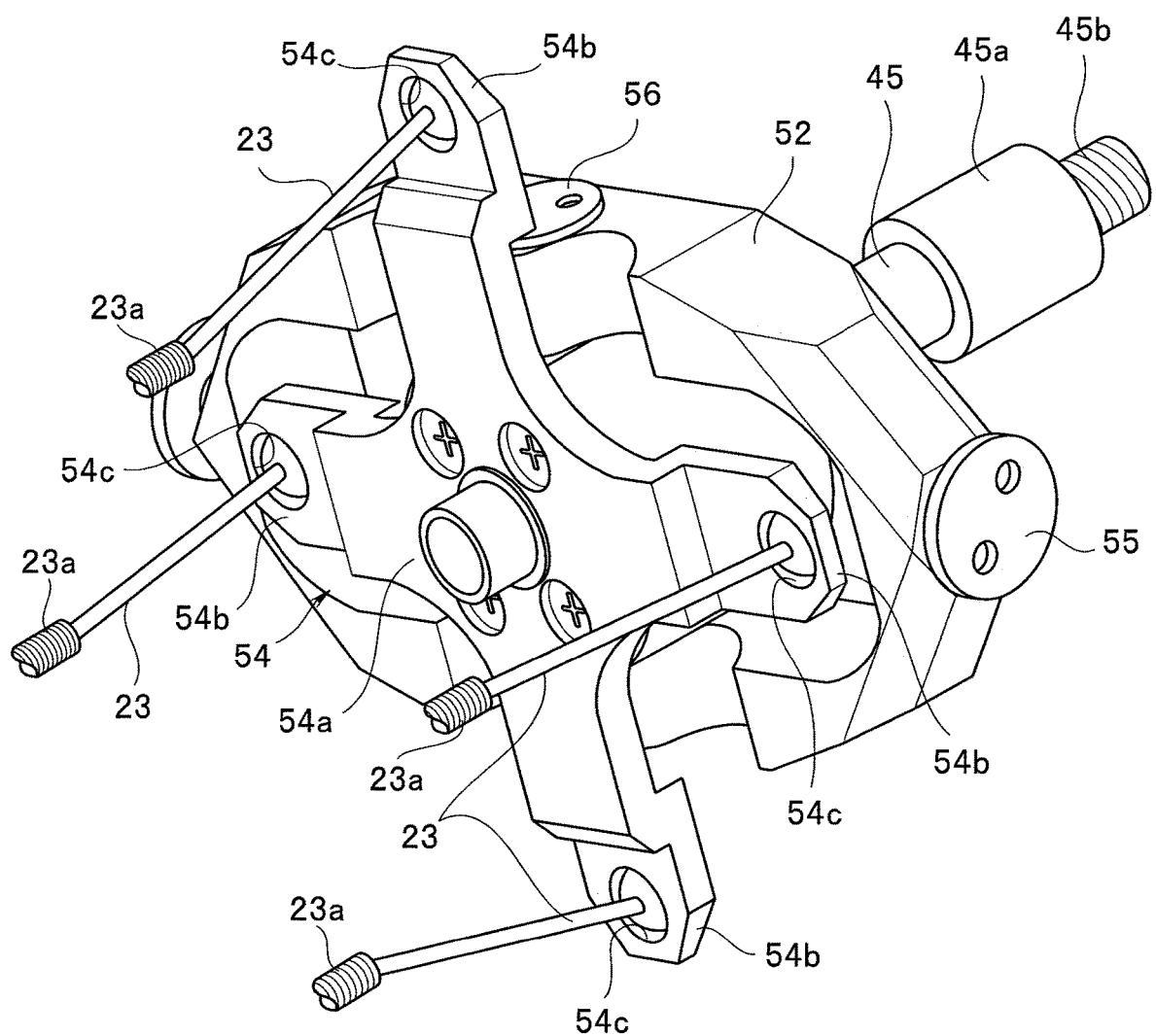
FIG. 4 is a perspective view illustrating an internal structure of a bending operation mechanism.

For example, as illustrated in FIG. 3, in the distal end portion 6, a distal end rigid portion 10 made of metal is provided. The distal end rigid portion 10 holds an image pickup unit 11 incorporating an image pickup device, such as a CCD or a CMOS, a light guide, which is not illustrated, a treatment instrument insertion channel 13, and the like.

Further, in the distal end portion 6, a distalmost bending piece 20 having a substantially cylindrical shape is fitted to the outer periphery at a proximal end side of the distal end rigid portion 10, and the outer periphery of the distalmost bending piece 20 is covered with a bent rubber 22. Wire fixing portions, which are not illustrated, are provided at four locations on the inner periphery of the distalmost bending piece 20 about an insertion axis O, and a distal end of any one of four traction wires 23 inserted into the insertion portion 2 is fixed to each wire fixing portion.

The bending portion 7 is configured to be actively bent in all directions, including the up, down, left, and right directions, about the insertion axis O depending on an operation input to the operation portion 3 by an operator such as a user.

Specifically, the bending portion 7 according to the present embodiment includes a bending piece pair 24 in which a plurality of bending pieces 25 are connected in a row. The respective bending pieces 25 are sequentially connected alternately by a pivot portion 25a disposed in the up-down direction of the insertion portion 2 and a pivot portion 25b disposed in the left-right direction of the insertion portion 2. Further, a predetermined bending piece 25 that configures the bending piece pair 24 is provided with a wire guide 26 for routing each traction wire 23 in the direction of the insertion axis O along an inner surface of the bending piece pair 24. Each bending piece 25 is rotated about the pivot portion 25a or the pivot portion 25b along with the traction or relaxation of each traction wire 23, thereby allowing the bending portion 7 to be actively bent in any direction, including the up, down, left, and right directions.

Note that in the present embodiment, the up, down, left, and right directions of the insertion portion 2 are, for example, directions defined by being associated with up, down, left, and right directions of an image picked up by the image pickup unit 11.

A signal cable 11a extending from the image pickup unit 11, the light guide, and the treatment instrument insertion channel 13 are inserted into the bending piece pair 24. The outer periphery of the bending piece pair 24 is covered with the bent rubber 22 extending from the side of the distal end portion 6.

The flexible tube portion 8 is configured using a tubular member that has flexibility and can be passively bent. The above-described signal cable 11a, light guide, and treatment instrument insertion channel 13, and the like (which are not illustrated) are inserted into the flexible tube portion 8.

The operation portion 3 includes a bend preventing portion 30 connected to the flexible tube portion 8 in a state where the bend preventing portion covers the proximal end of the flexible tube portion 8, a grasping portion 31 that is joined with the bend preventing portion 30 and can be grasped by a hand of a user or the like, and an operation portion main body 32 that is connected to the proximal end side of the grasping portion 31. Note that in the present embodiment, the direction and the like about the insertion axis O in the operation portion 3 are defined based on a state where the grasping portion 31 is grasped by the user or the like. Specifically, in the operation portion 3, the front, back, left, and right directions (a front surface, a back surface, a left side, a right side, and the like) are defined in directions perpendicular to the insertion axis O based on a state where the user or the like suspends the insertion portion 2 and grasps the grasping portion 31 in the forward direction.

As illustrated in FIG. 1, the grasping portion 31 according to the present embodiment is formed in a bilaterally symmetrical shape with respect to the insertion axis O (central axis), which enables the user or the like to grip the grasping portion in the same manner with the left or right hand of the user or the like.

The distal-end-side front surface of the grasping portion 31 is provided with a treatment instrument insertion portion 35. The treatment instrument insertion portion 35 includes a treatment instrument insertion opening 35a into which various treatment instruments (not illustrated) are inserted. In the operation portion 3, the treatment instrument insertion channel 13 communicates with the treatment instrument insertion opening 35a through a branch member that is not illustrated. A forceps plug (not illustrated) that is a lid member for closing the treatment instrument insertion opening 35a is removably mounted on the treatment instrument insertion portion 35.

The operation portion main body 32 is formed using a hollow member that is formed substantially in a partially spherical shape swelling mainly toward the left and right sides and toward the front side at the proximal end side of the grasping portion 31.

An operation button group 40 for executing various functions of the endoscope 1 is disposed on the front surface side of the operation portion main body 32. The operation button group 40 includes, for example, a suction button 41a that projects from a suction valve 41 that is removably mounted on the operation portion main body 32, and two button switches 42 to which any function can be allocated from among various functions for the endoscope 1.

Meanwhile, a bending lever 45 serving as a lever is disposed on the back surface side of the operation portion main body 32. The bending lever 45 configures a bending operation mechanism 50 for allowing the bending portion 7 to be bent, and can be tilted in all directions, including the first direction (up direction), the second direction (down direction), the third direction (left direction), and the fourth direction (right direction), which are associated with the up, down, left, and right directions, respectively, of the bending portion 7.

Further, a universal cord 4 extends from one side portion (e.g., a left side portion) of the operation portion main body 32.

In this case, the left and right shapes of the operation portion main body 32 are symmetrically swelled with respect to the insertion axis O and guiding recessed portions 32a for guiding the operation button group 40 by the forefinger or the like of the user who has grasped the grasping portion 31 are formed on left and right side surfaces at the distal end side of the operation portion main body 32.

The universal cord 4 is a composite cable that reaches the operation portion 3 from the distal end portion 6 through the inside of the insertion portion 2, allows insertion of various signal lines and the like extending from the operation portion 3, allows insertion of a light guide of a light source apparatus (not illustrated), and allows insertion of an air/water feeding tube extending from the air/water feeding apparatus (not illustrated).

The endoscope connector 5 has a configuration in which an electric connector portion 5a to which a signal cable that connects a video processor (not illustrated), which is an external device is connected is provided on a side surface, and a light source connector portion 5b to which a light guide and an electric cable that connect the light source apparatus, which is an external device, are connected is provided.

Next, the configuration of the bending operation mechanism 50 provided on the operation portion main body 32 will be described in more detail.

As illustrated in FIGS. 4 to 7, the bending operation mechanism 50 includes a housing 51 that is fixed to the operation portion main body 32, a rotation frame 52 that is rotatably (swingably) supported in the housing 51, a base member 53 that is rotatably (swingably) supported in the rotation frame 52, a wire traction member 54 that is fixed to one end of the base member 53, and a bending lever 45 that projects from the other end of the base member 53.

The housing 51 is configured using a member having a substantially cylindrical shape. Shaft holes 51a that are opposed to each other are formed in the peripheral wall of the housing 51.

The rotation frame 52 is configured using, for example, a frame body formed in a substantially rectangular shape. In the rotation frame 52, a pair of screw holes 52a opposed to each other is formed at the center of both end portions in the longitudinal direction. A pair of shaft holes 52b opposed to each other at the center of both end portions in the lateral direction is formed in the rotation frame 52. Further, screws 55 that are inserted into each shaft hole 51a of the housing 51 is screwed into the respective screw holes 52a, so that the rotation frame 52 is pivotally supported turnably with respect to the housing 51.

Figure 5:
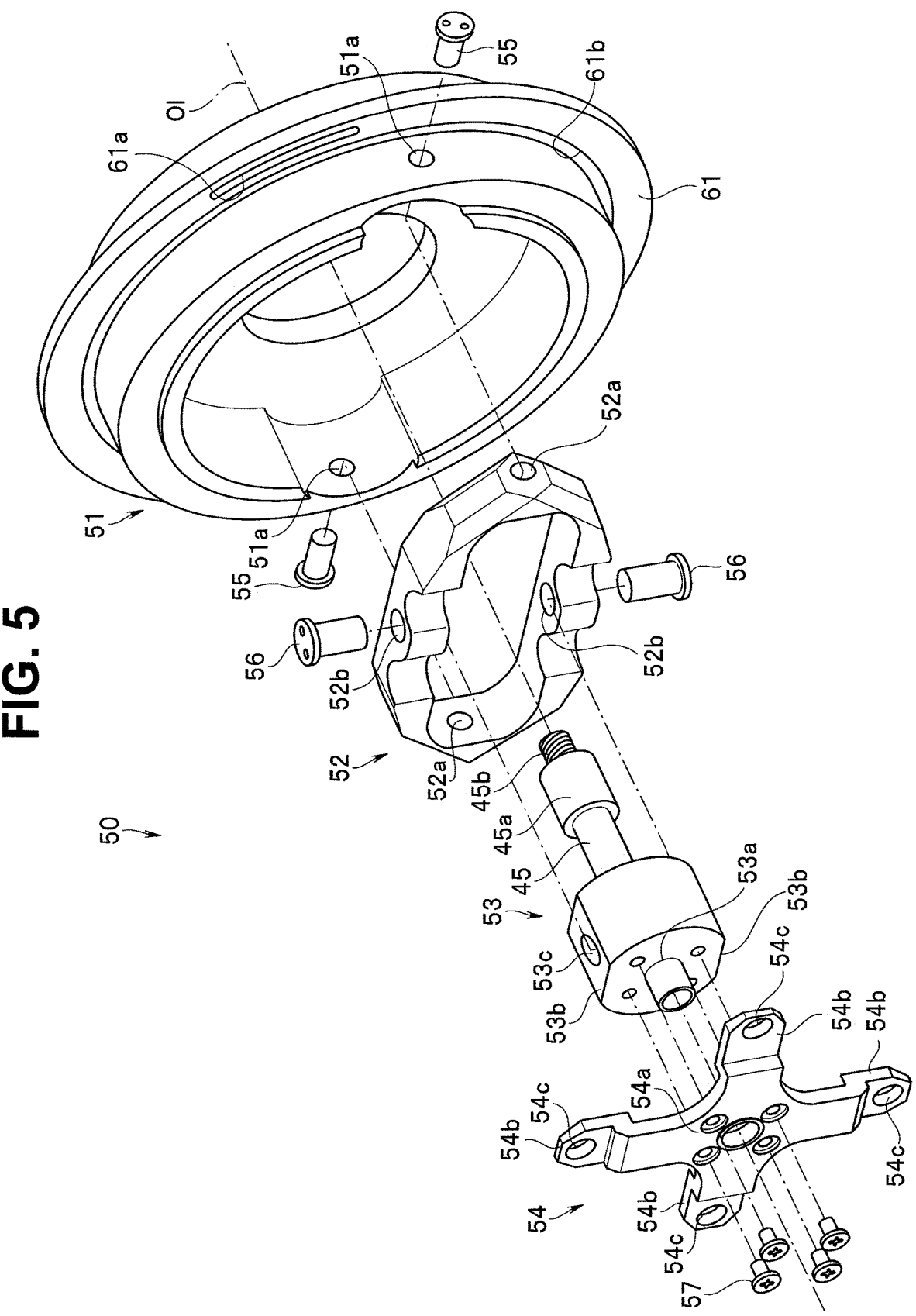
FIG. 5 is an exploded perspective view illustrating the bending operation mechanism.

The base member 53 is formed of a member having a substantially cylindrical shape. A fitting hole 53a is formed at a central portion of the base member 53, and the fitting hole 53a is connected such that the proximal end of the bending lever 45 is fitted into the fitting hole. A pair of flat portions 53b opposed to each other is formed on the peripheral portion of the base member 53. The pair of flat portions 53b opposed to each other is formed on the peripheral portion of the base member 53, and screw holes 53c (only one of the screw holes 53c is illustrated in FIG. 5) opposed each other is formed in the flat portions 53b. The screws 56 inserted into the respective shaft holes 52b of the rotation frame 52 are screwed into the respective screw holes 53c, thereby allowing the base member 53 to be pivotally supported turnably with respect to the rotation frame 52. Thus, the base member 53 is supported by the housing 51 through the rotation frame 52, thereby enabling the bending lever 45 connected to the base member 53 to be tilted in any direction.

The wire traction member 54 is configured using a plate-like member with arm portions 54b extending in four different directions, respectively. More specifically, in the present embodiment, the wire traction member 54 is configured using a plate-like member that is formed in a cross shape and has a configuration in which an angle formed between the adjacent arm portions 54b is set to 90 degrees, and a central portion 54a is fixed to the proximal end face of the base member 53 through a screw 57. Specifically, the bending lever 45 is connected to the wire traction member 54 through the base member 53. Each wire fixation hole 54c is formed at the extending end side of each arm portion 54b. The proximal end side of each traction wire 23 extending from the insertion portion 2 side is fixed to the corresponding wire fixation hole 54c. With this configuration, the wire traction member 54 enables the predetermined traction wire 23 to be retracted by a predetermined traction amount depending on the tilted state of the bending lever 45. Note that the angle formed between the arm portions 54b is not limited to 90 degrees, but can be arbitrarily changed, for example, within a range of ±30 based on the 90 degrees.

Figure 6:
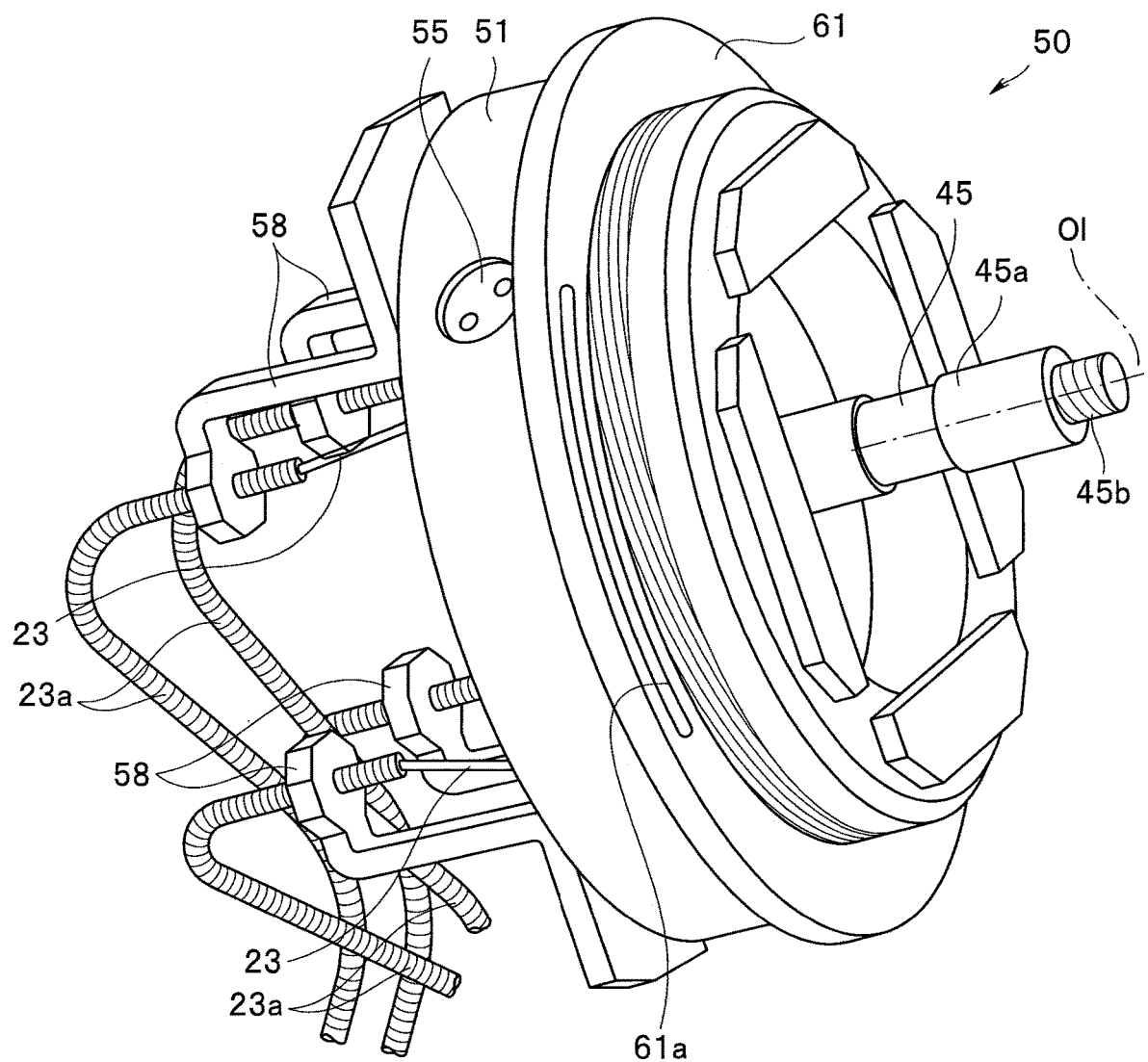
FIG. 6 is a perspective view illustrating the bending operation mechanism.

In this case, for example, as illustrated in FIG. 6, the housing 51 of the bending operation mechanism 50 is provided with four stays 58, and the proximal end side of each guide coil 23a is held in the corresponding stay 58. Each traction wire 23 is routed into the flexible tube portion 8 from the inside of the operation portion 3 in a state where each traction wire 23 is inserted into the corresponding guide coil 23a. Thus, each traction wire 23 is allowed to advance or retract (relaxation or traction operation) in conjunction with the tilting operation of the bending lever 45 without interfering with another internal component or the like.

Figure 7:
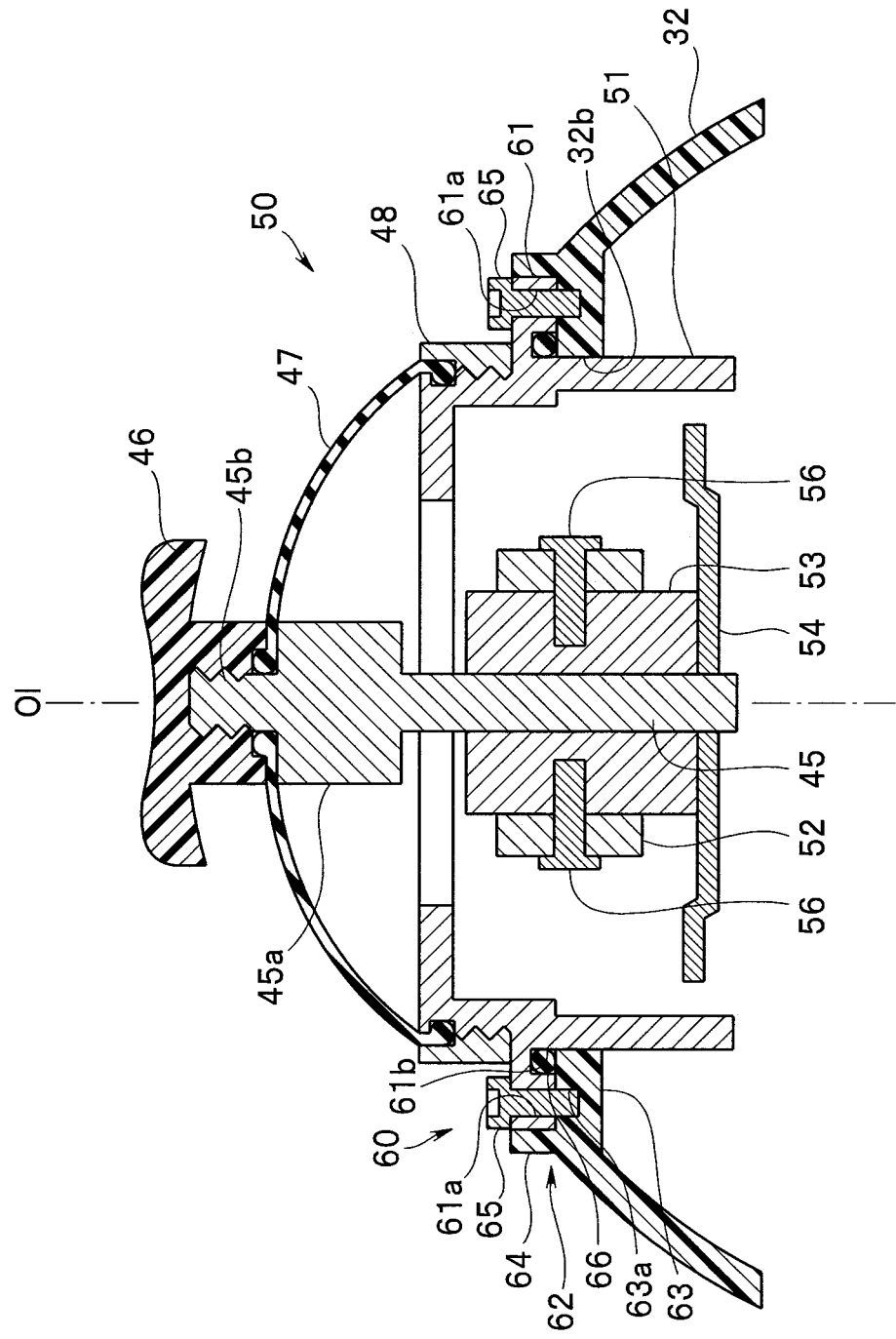
FIG. 7 is a sectional view illustrating a major portion of each of the bending operation mechanism and a variable fixation mechanism.

As illustrated in FIG. 7, the bending lever 45 projects to the outside of the housing 51. The bending lever 45 is provided with a thick portion 45a at a projecting end side, and an external thread portion 45b is formed at the projecting end side of the thick portion 45a.

A finger-rest portion 46 with which the thumb or the like of the user can be brought into contact is fixed to the external thread portion 45b of the bending lever 45 through a screw.

An external cover 47 for sealing the space between the bending lever 45 and the housing 51 in a liquid-tight manner is provided on the outer periphery of the bending lever 45.

Specifically, for example, as illustrated in FIG. 7, the external cover 47 is configured using a resin mold that extends in substantially a dome shape from one end side to the other end side. An end portion of the external cover 47 is nipped between the thick portion 45a of the bending lever 45 and the finger-rest portion 46, thereby being connected in a liquid-tight state at the outer periphery of the bending lever 45. Meanwhile, a stopper ring 48 is screwed at the outer periphery of the housing 51, and the other end portion of the external cover 47 is nipped between the housing 51 and the stopper ring 48, thereby being connected in a liquid-tight state at the outer periphery of the housing 51.

In the bending operation mechanism 50 having a configuration as described above, the wire traction member 54 side is accommodated in the operation portion main body 32 through an orifice portion 32b that is formed in the operation portion main body 32.

Further, the bending operation mechanism 50 is fixed in a state where the bending operation mechanism can be appropriately displaced with respect to the operation portion main body 32 through a variable fixation mechanism 60 configured between the housing 51 and the operation portion main body 32.

Specifically, the variable fixation mechanism 60 includes an outward flange 61 provided on the outer peripheral surface of the housing 51, and a flange accommodation chamber 62 provided on the operation portion main body 32.

The outward flange 61 is configured using, for example, an annular flange that is formed at the entire circumference of the outer peripheral surface of the housing 51.

The outward flange 61 is provided with a pair of long holes 61a that penetrates through the outward flange in the thickness direction. Each long hole 61a is formed in a partially arc shape about a point on the central axis OI in a neutral state where the bending lever 45 is not tilted, and is disposed at a position that is rotationally symmetrical to the central axis OI.

On the back surface side of the outward flange 61, an annular seal groove 61b is provided in the inner side of the long holes 61a, and a seal ring 66, such as an O-shaped ring, is held in the seal groove 61b.

The flange accommodation chamber 62 includes an inward flange 63 that is formed in the orifice portion 32b of the operation portion main body 32, and a wall portion 64 that is provided at the outer periphery of the inward flange 63.

The inward flange 63 is an annular flange having an inner diameter and an outer diameter that are substantially the same as those of the outward flange 61, and is formed at the entire circumference on the inside of the orifice portion 32b.

The inward flange 63 is provided with a pair of screw holes 63a corresponding to the long holes 61a.

The wall portion 64 has a height that is substantially equal to, for example, the thickness of the outward flange 61, and is formed in a cylindrical shape having an inner diameter that is substantially equal to the outer diameter of the outward flange 61.

As illustrated in FIGS. 7 to 10, the outward flange 61 is slidably accommodated in the flange accommodation chamber 62 configured as described above. A bolt 65 serving as an engagement pin, which is formed of a hexagon socket head cap screw or the like, is inserted into the long holes 61a of the outward flange 61. Further, the bolt 65 is screwed into the screw holes 63a, so that the bending operation mechanism 50 is fixed to the operation portion main body 32.

Figure 8:
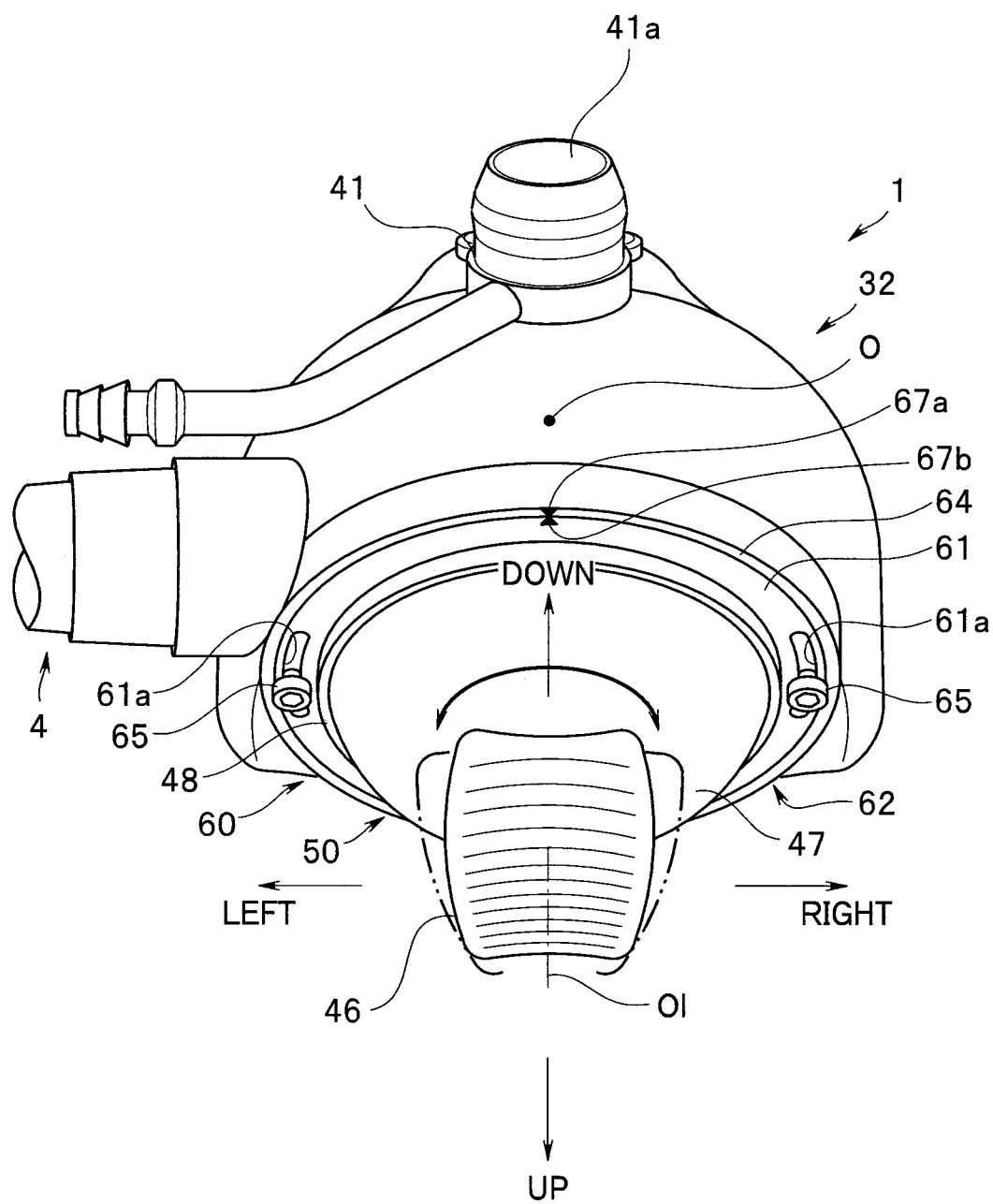
FIG. 8 is a perspective view illustrating the bending operation mechanism fixed to an operation portion main body.
Figure 9:
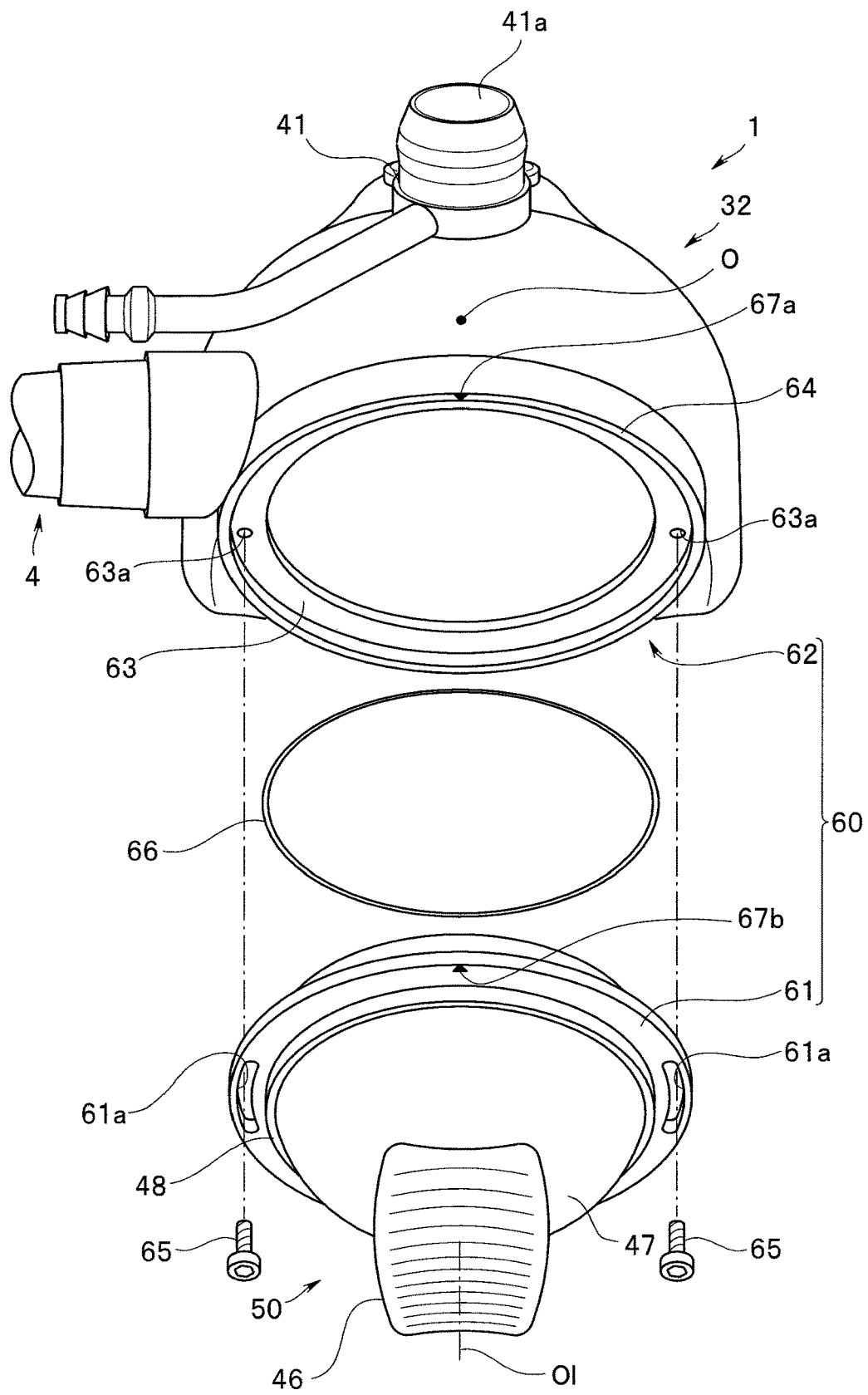
FIG. 9 is an exploded perspective view illustrating the variable fixation mechanism configured between the operation portion main body and the bending operation mechanism.

In this case, as illustrated in FIGS. 8 and 9, for example, positioning indices 67a and 67b are provided on the surface of the outward flange 61 and on the end face of the wall portion 64. The indices 67a and 67b are aligned so that the rotation position about the central axis OI in the first to fourth directions, which are set for the bending lever 45, with respect to the operation portion 3 (operation portion main body 32) is set to a preset reference position (neutral position).

Further, the rotation position of the positioned bending lever 45 about the central axis OI with respect to the operation portion main body 32 can be arbitrarily displaced depending on the user or the like by making an adjustment on the variable fixation mechanism 60.

In other words, the rotation position about the central axis O in the first to fourth directions set for the bending lever 45 can be adjusted by releasing the fastened state of the bolt 65 in the variable fixation mechanism 60 and by rotating the housing 51 within a range allowed by the long holes 61a.

Figure 10:
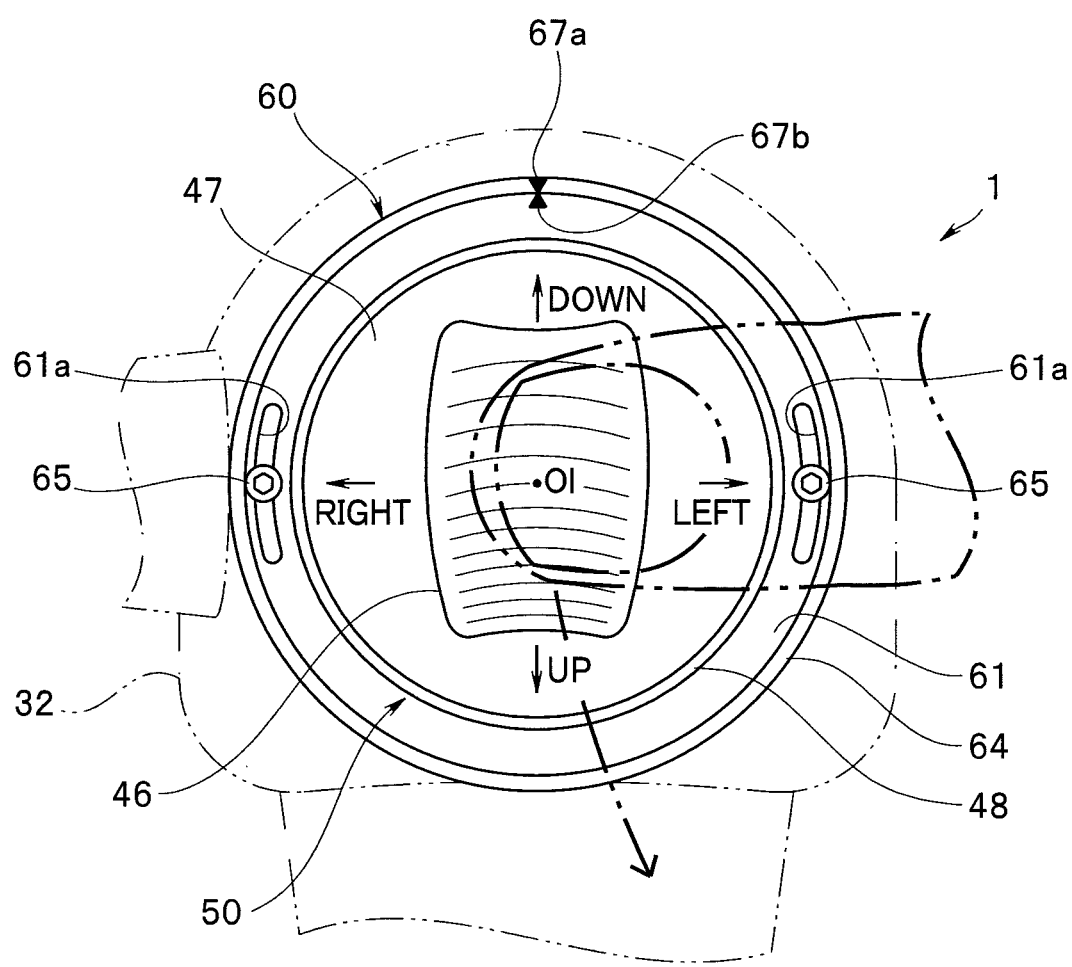
FIG. 10 is a plan view illustrating the bending operation mechanism fixed to a reference position with respect to the operation portion main body.
Figure 11:
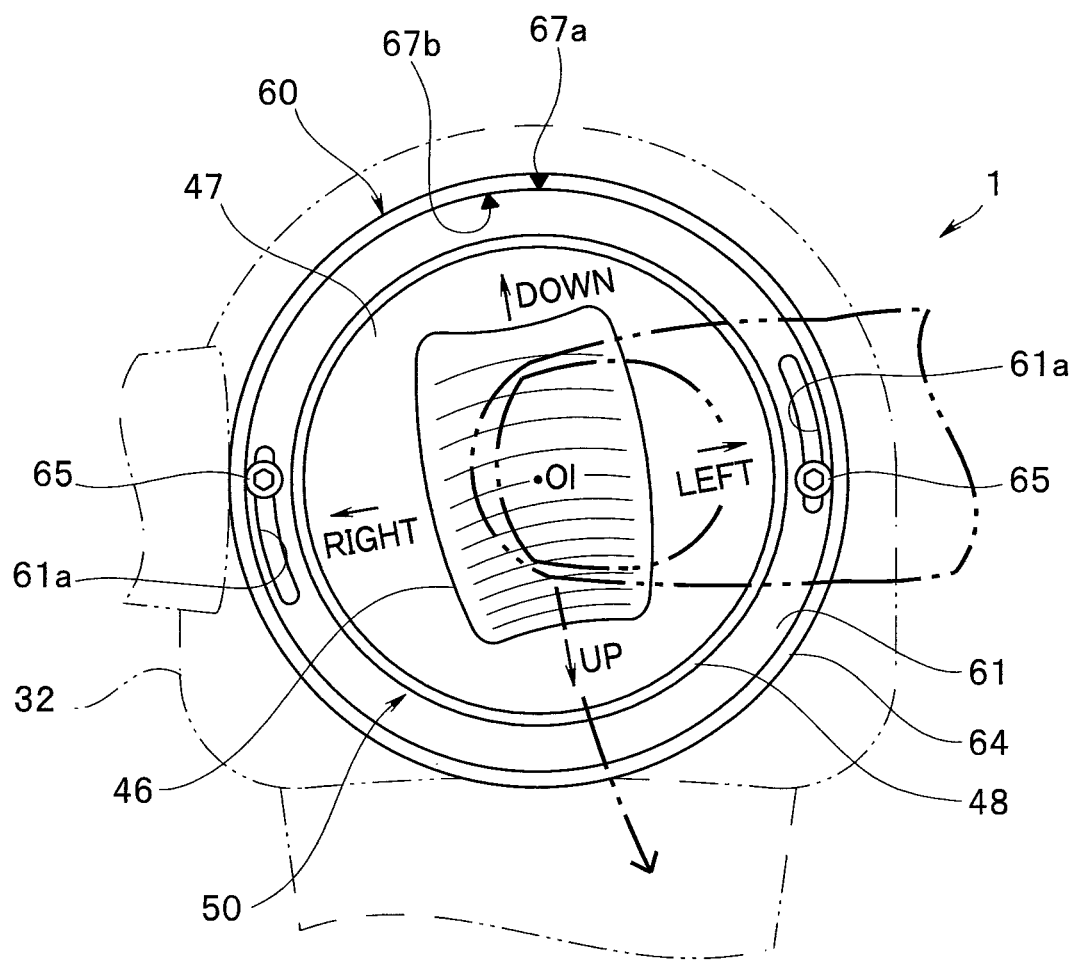
FIG. 11 is a plan view illustrating the bending operation mechanism fixed at a position displaceable from the reference position with respect to the operation portion main body.

With this configuration, a specific direction in which the bending portion 7 is often tilted by the user or the like, for example, during a bending operation in an inspection or the like using the endoscope 1 can be matched with a trajectory of a finger of the user or the like that operates the bending lever 45. Specifically, for example, as illustrated in FIGS. 10 and 11, when the bending portion 7 is often bent upward by the user or the like, the first direction corresponding to the upward bending can be matched with the trajectory of the finger of the user or the like that operates the bending lever 45.

According to the embodiment as described above, the endoscope 1 including the bending operation mechanism 50 including a single bending lever 45 configured to be tilted in all directions including a first direction, a second direction, a third direction, and a fourth direction corresponding to bend directions of the bending portion 7 in the up, down, left, and right directions is provided with the variable fixation mechanism 60 that is configured between the bending operation mechanism 50 and the operation portion main body 32 (operation portion 3) and fixes the bending operation mechanism 50 in a state where the bending operation mechanism 50 can be displaced with respect to the operation portion main body 32, thereby making it possible to accurately perform a bending operation in a specific direction on the joystick-type bending lever 45.

Figure 12:
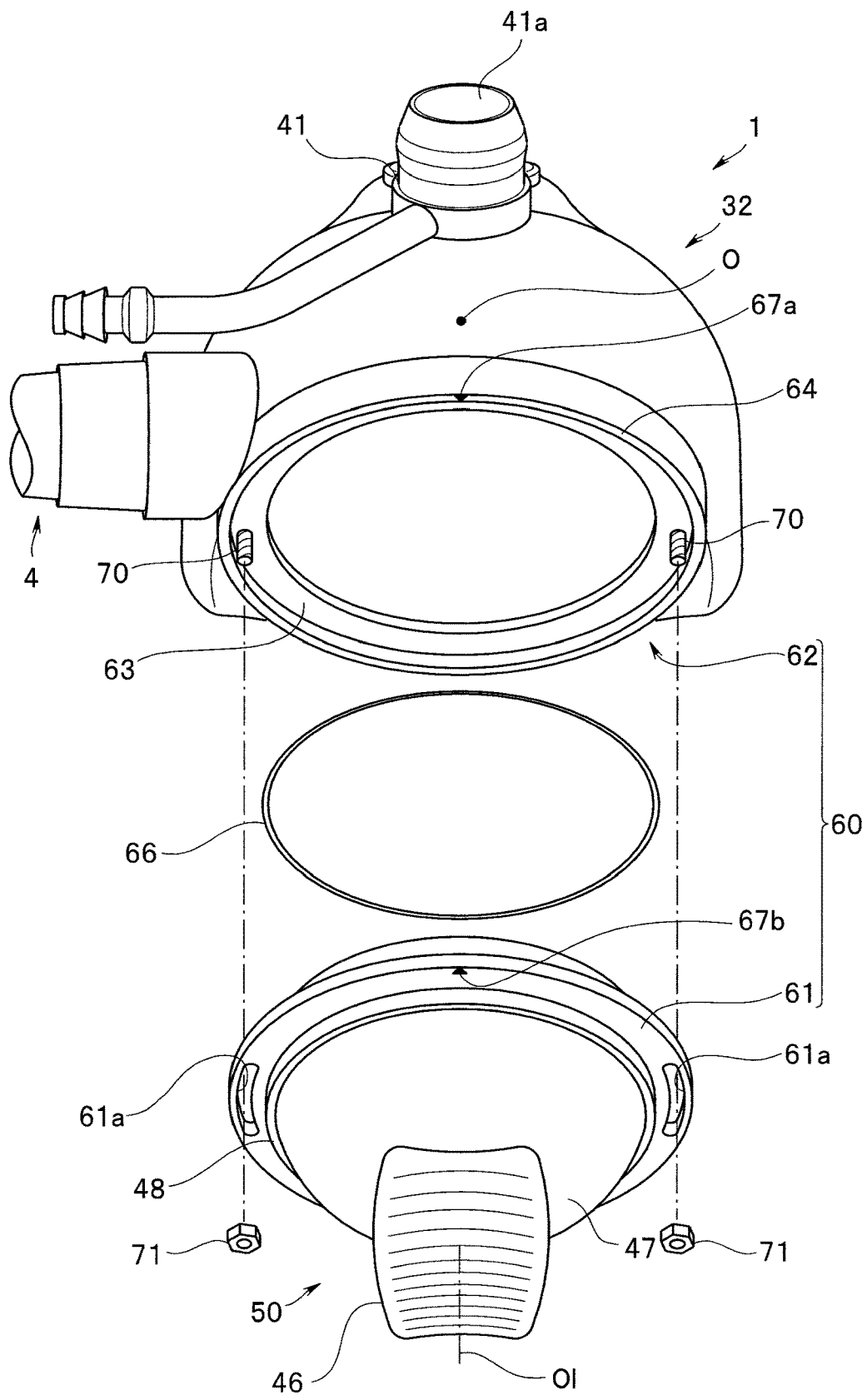
FIG. 12 is an exploded perspective view illustrating a variable fixation mechanism configured between an operation portion main body and a bending operation mechanism according to a first modification.

In this case, for example, as illustrated in FIG. 12, the variable fixation mechanism 60 can be configured by allowing bolts 70 each serving as an engagement pin to project toward the inward flange 63, instead of using the configuration in which the bolt 65 is screwed into the screw hole 63a of the inward flange 63. In this case, the bending operation mechanism 50 can be fixed in a displaceable manner by screwing nuts 71 into the respective bolts 70 inserted into the long holes 61*a*.

Figure 13:
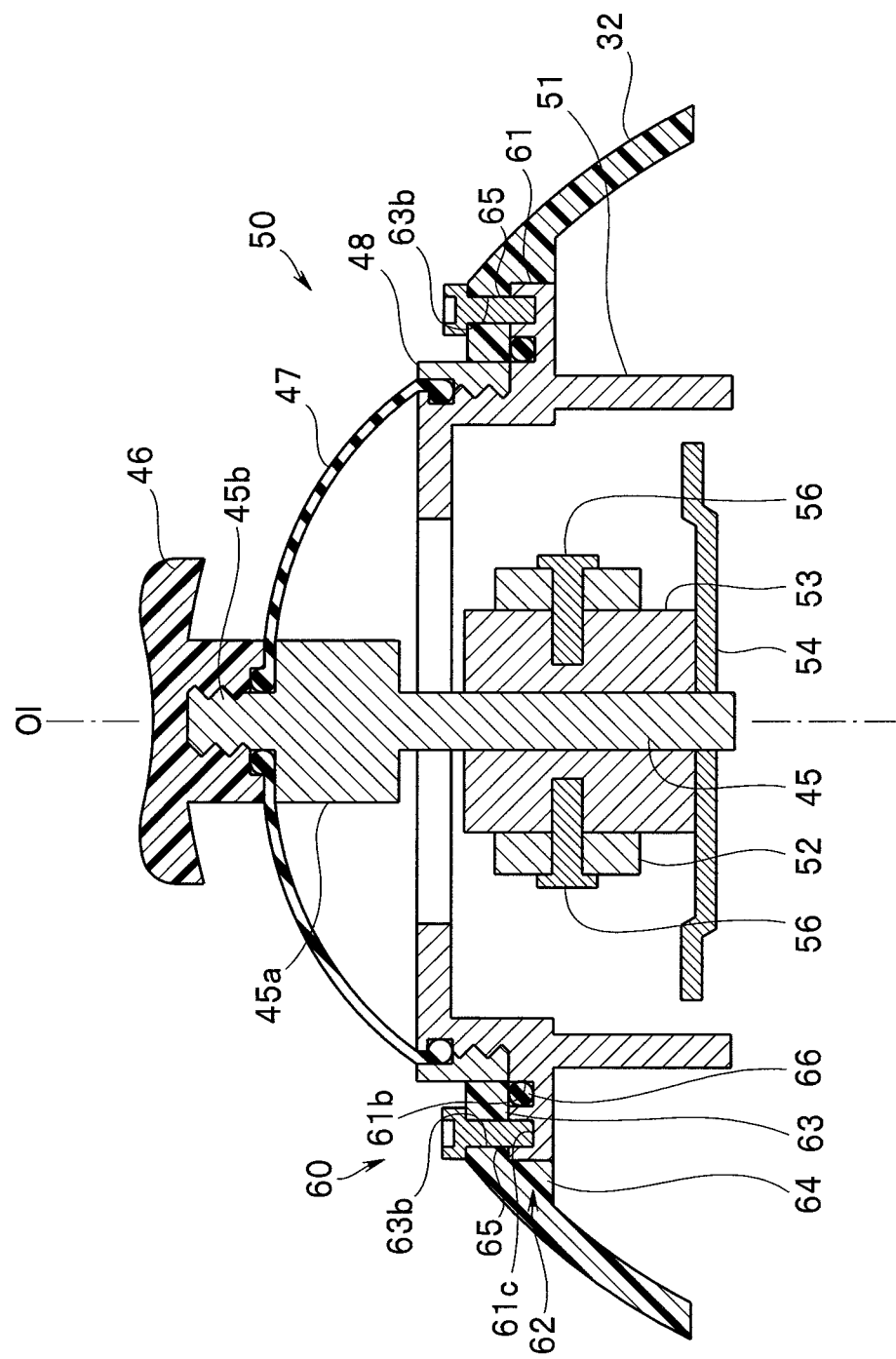
FIG. 13 is a sectional view illustrating a major portion of each of a bending operation mechanism and a variable fixation mechanism according to a second modification.

As illustrated in FIG. 13, for example, the layout of the outward flange 61 provided on the bending operation mechanism 50 and the flange accommodation chamber 62 provided on the operation portion main body 32 can be reversed.

In this case, the inward flange 63 that configures the flange accommodation chamber 62 is provided with long holes 63*b* and the outward flange 61 is provided with a screw hole 61*c*, thereby obtaining substantially the same advantageous effects as those of the above-described embodiment.

Figure 14:
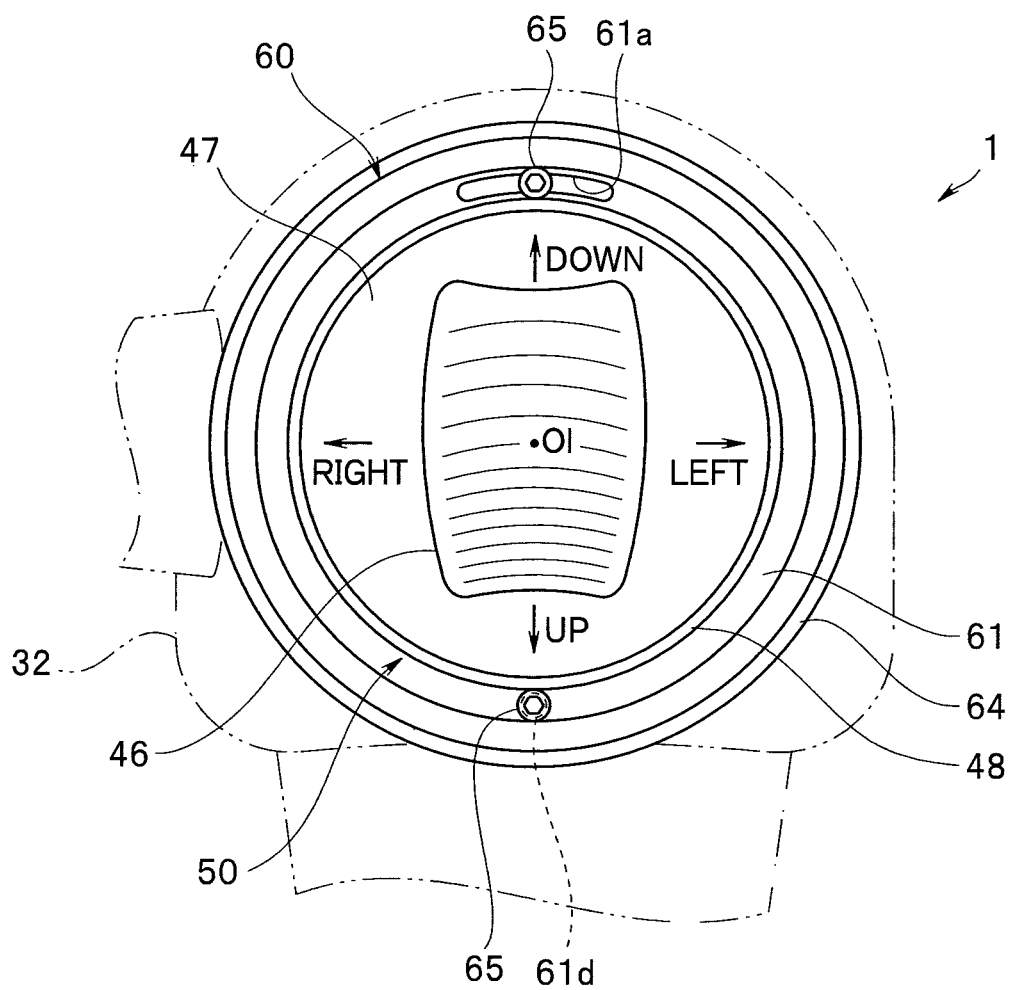
FIG. 14 is a plan view illustrating a bending operation mechanism fixed at a reference position with respect to an operation portion main body according to a third modification.
Figure 15:
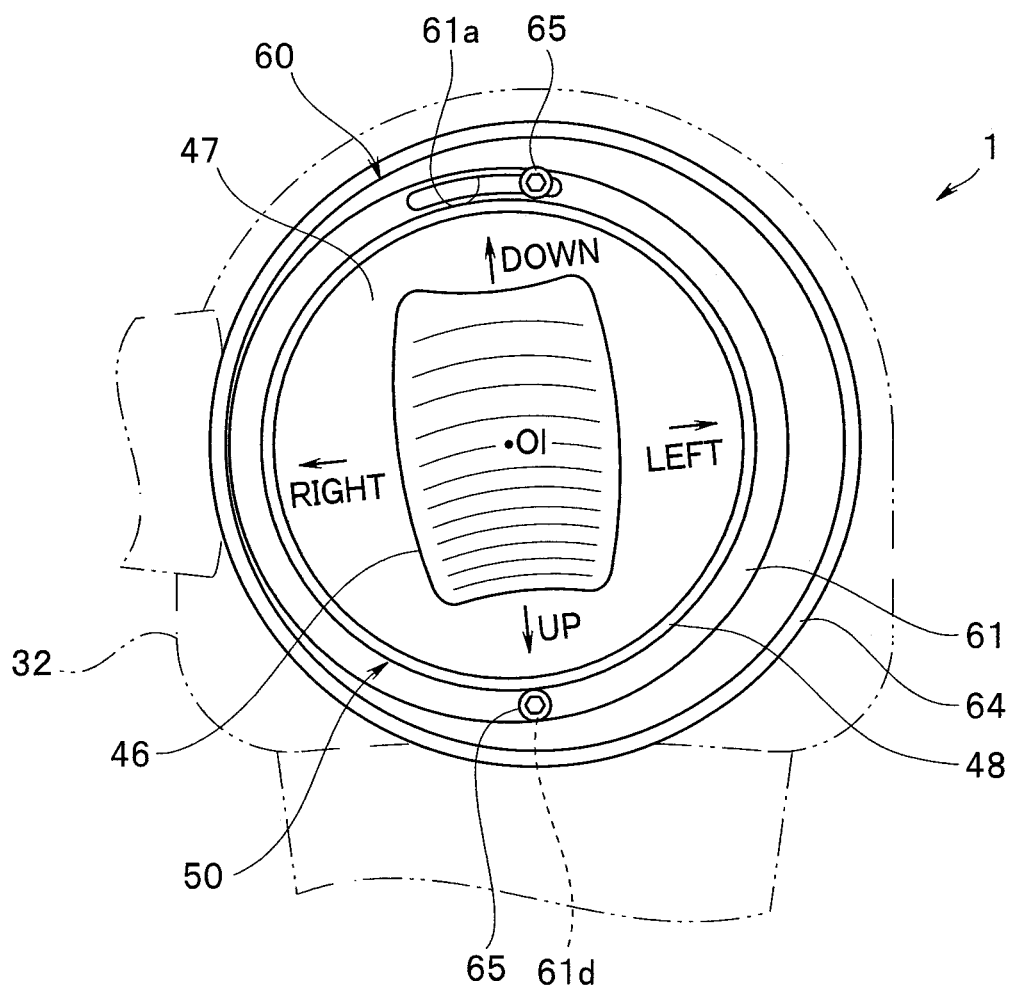
FIG. 15 is a plan view illustrating the bending operation mechanism fixed at a position displaceable from the reference position with respect to the operation portion main body according to the third modification.
Figure 16:
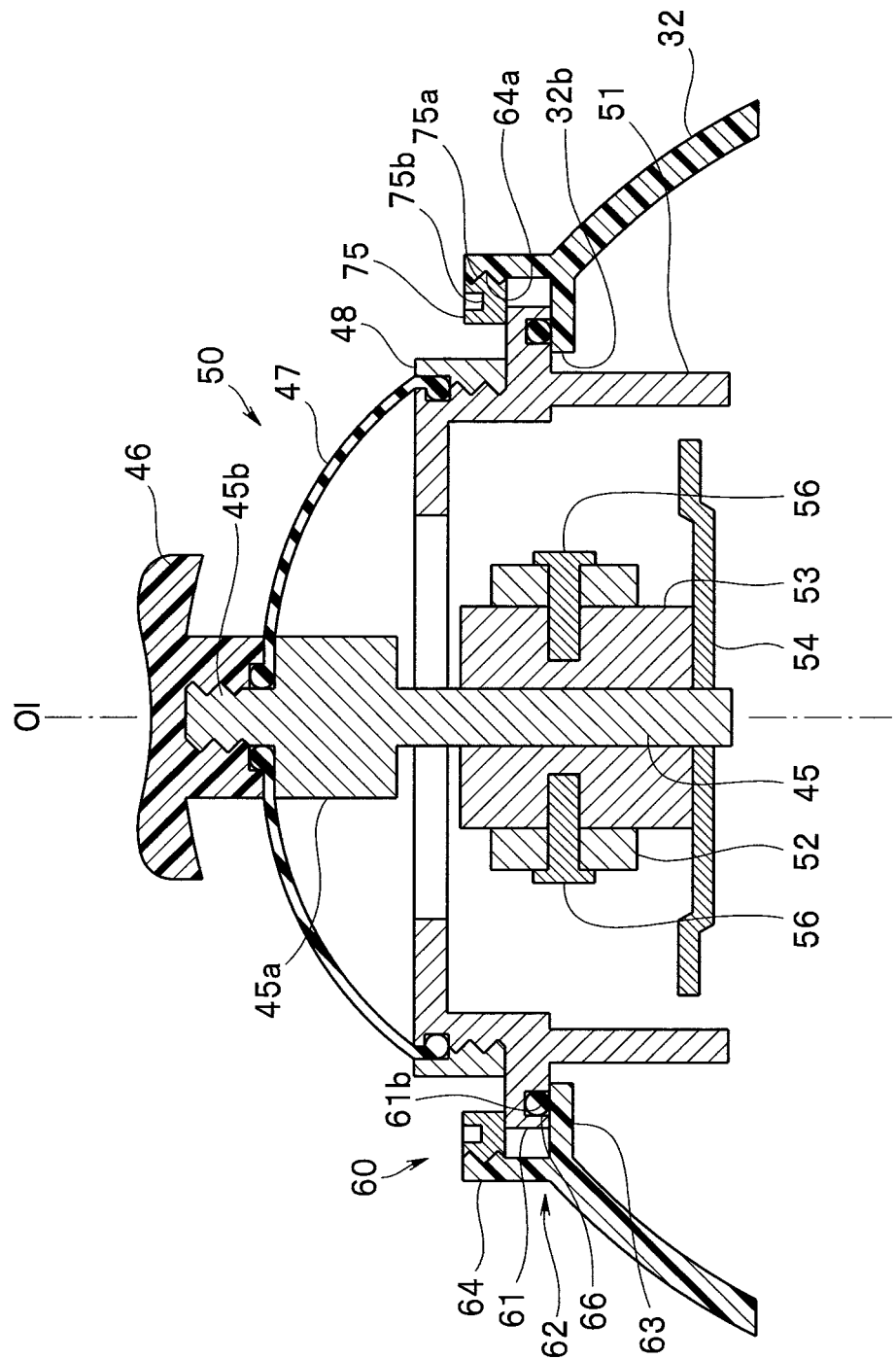
FIG. 16 is an exploded perspective view illustrating a variable fixation mechanism configured between an operation portion main body and a bending operation mechanism according to a fourth modification.
Figure 17:
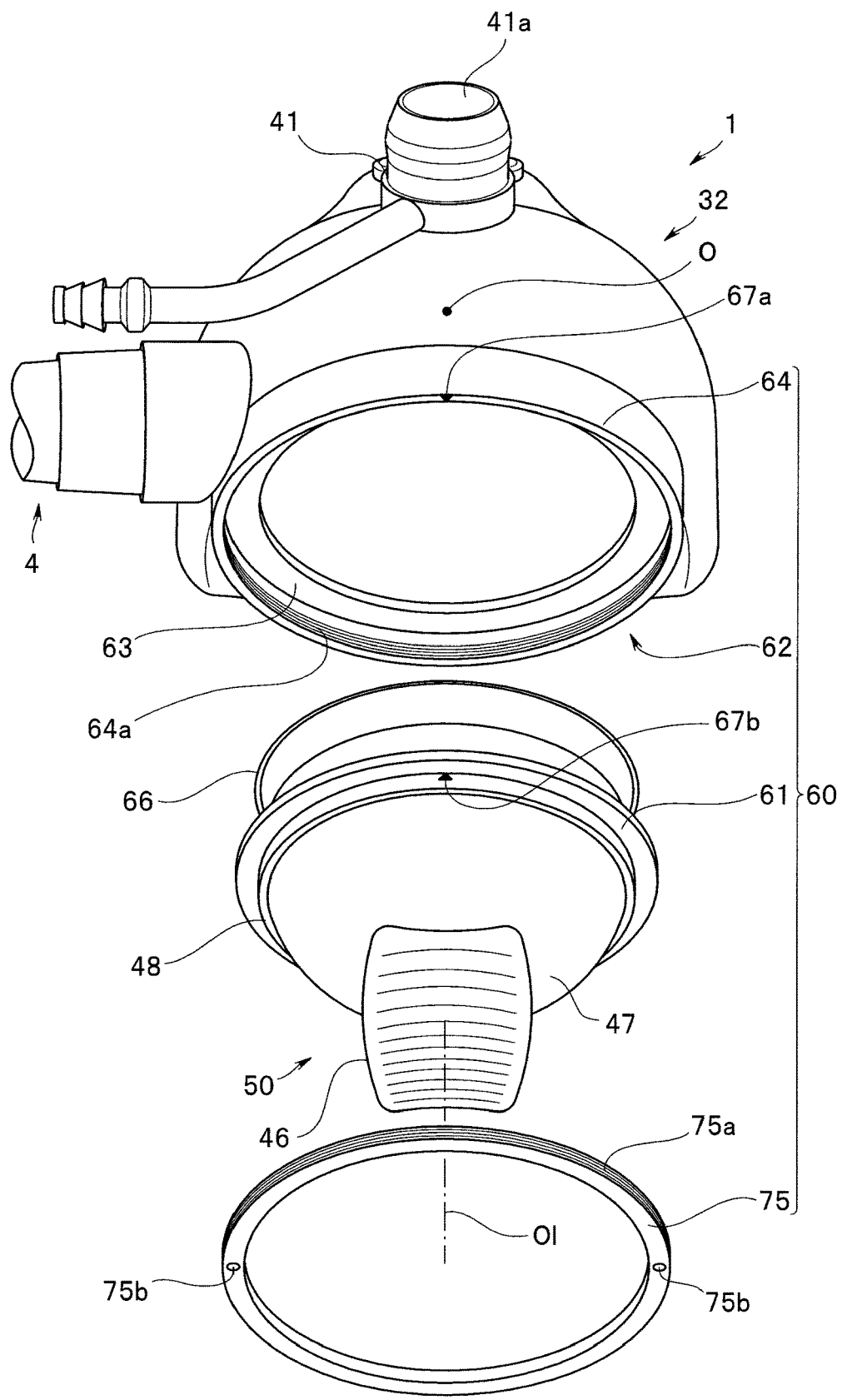
FIG. 17 is an exploded perspective view illustrating the variable fixation mechanism configured between the operation portion main body and the bending operation mechanism according to the fourth modification.

As illustrated in FIGS. 14 and 15, for example, one of the pair of long holes 61*a* provided in the outward flange 61 can be replaced with a shaft receiving hole 61*d* and the inner diameter of the wall portion 64 can be set to a value that is sufficiently larger than the outer diameter of the outward flange 61. According to this configuration, the bending operation mechanism 50 can be displaced so that the bending operation mechanism 50 can swing with the shaft receiving hole 61*d* as a fulcrum.

As illustrated in FIGS. 16 to 19, for example, a pressing member 75 that is formed of an annular plate is assembled on the wall portion 64 of the flange accommodation chamber 62 and the outward flange 61 is nipped between the pressing member 75 and the inward flange 63, thereby making it possible to configure the variable fixation mechanism 60 that fixes the bending operation mechanism 50 in a displaceable manner.

Specifically, in the present modification, the inner diameter of the wall portion 64 that configures the flange accommodation chamber 62 is set to a value that is sufficiently larger than the outer diameter of the outward flange 61.

An internal thread portion 64*a* is provided on the inner periphery of the wall portion 64.

An external thread portion 75*a* that can be screwed into the internal thread portion 64*a* is provided on the outer periphery of the pressing member 75. Note that in the drawings, reference symbol 75*b* denotes an engagement hole with which a jig for assembling the pressing member 75 on the wall portion 64 engages.

In the variable fixation mechanism 60 having a configuration as described above, the external thread portion 75*a* of the pressing member 75 is screwed into the internal thread portion 64*a* of the wall portion 64 and the outward flange 61 is nipped between the pressing member 75 and the inward flange 63, thereby making it possible to fix the bending operation mechanism 50 to the operation portion main body 32.

Figure 18:
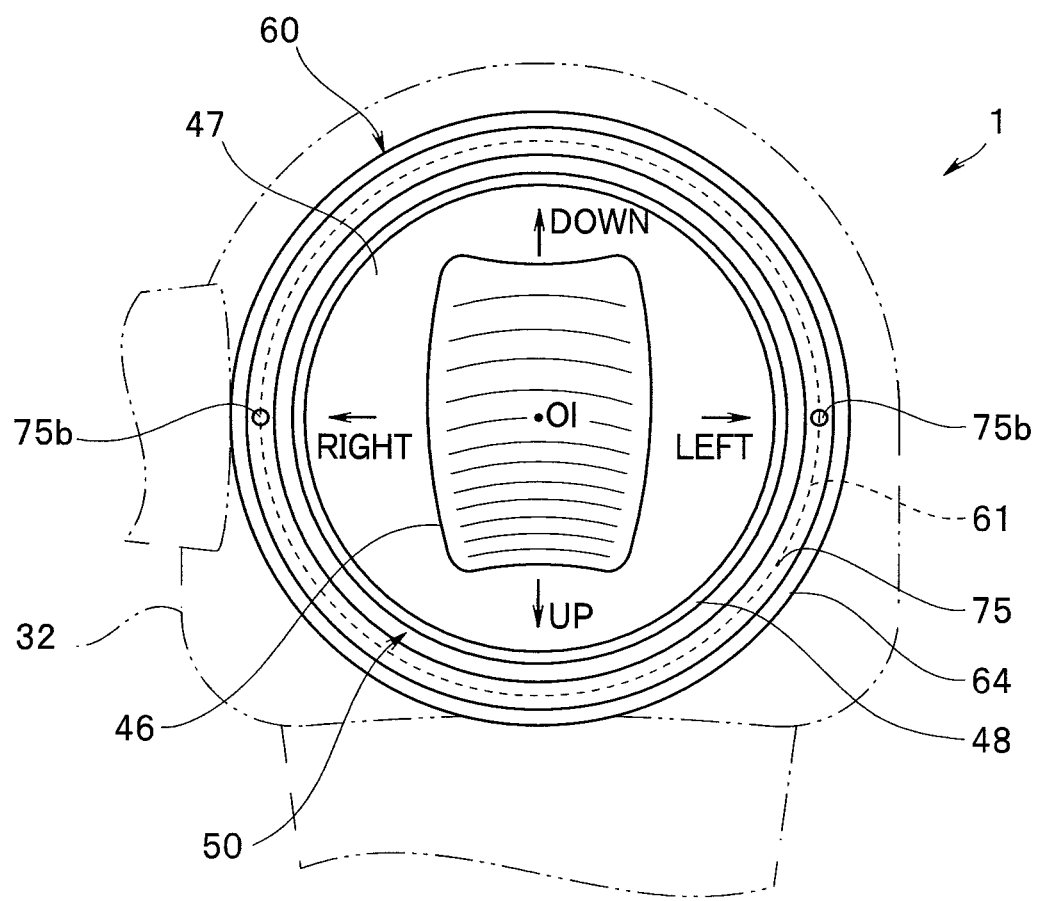
FIG. 18 is a plan view illustrating the bending operation mechanism fixed at the reference position with respect to the operation portion main body according to the fourth modification.
Figure 19:
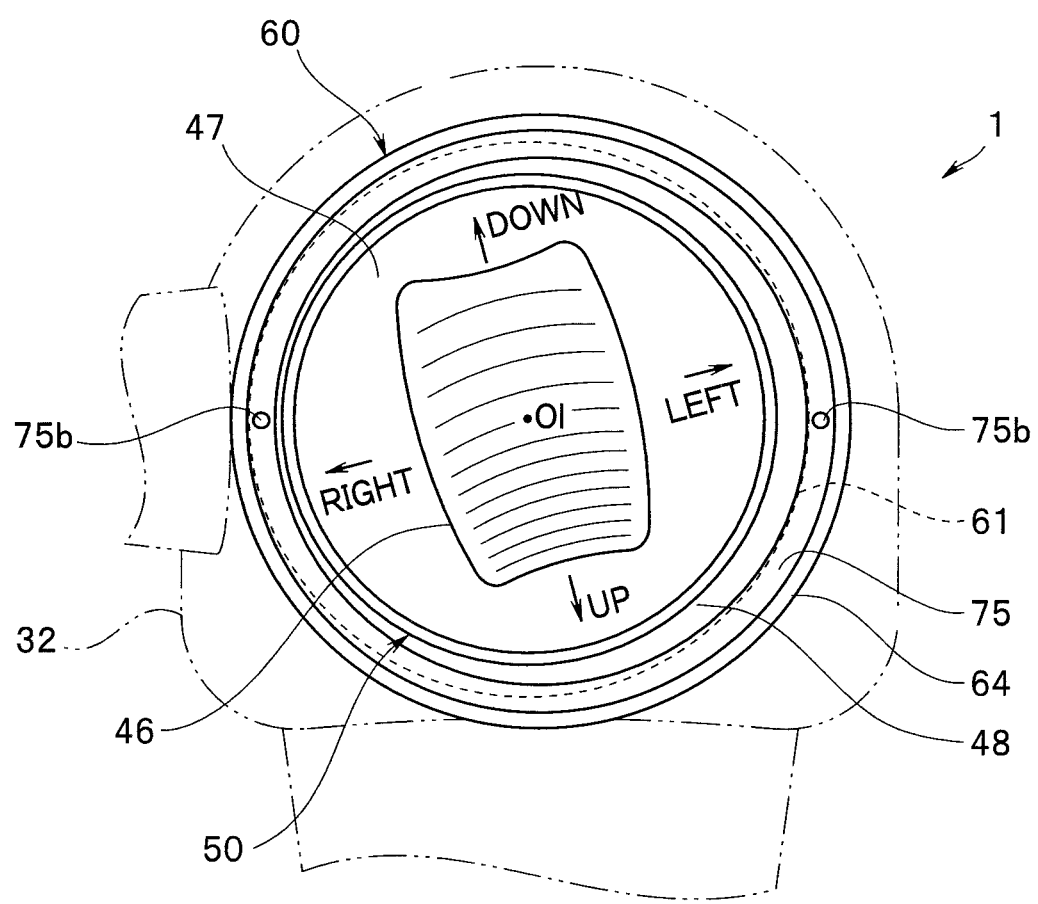
FIG. 19 is a plan view illustrating the bending operation mechanism fixed at a position displaceable from the reference position with respect to the operation portion main body according to the fourth modification.

Further, in the variable fixation mechanism 60, the state where the external thread portion 75*a* is screwed into the internal thread portion 64*a* is released, thereby enabling the first, second, third, and fourth directions of the bending lever 45 to be displaced with respect to the operation portion main body 32. Specifically, as illustrated in FIGS. 18 and 19, in the variable fixation mechanism 60 according to the present modification, the bending operation mechanism 50 is rotated about the central axis OI and the bending operation mechanism 50 is allowed to slide in the direction vertical to the central axis OI, thereby making it possible to displace the bending operation mechanism 50 with respect to the operation portion main body 32.

Note that, in the variable fixation mechanism 60 according to the present modification, only one of the operation of rotating the bending operation mechanism 50 about the central axis OI and the operation of allowing the bending operation mechanism 50 to slide in the direction vertical to the central axis OI can be performed.

Figure 20:
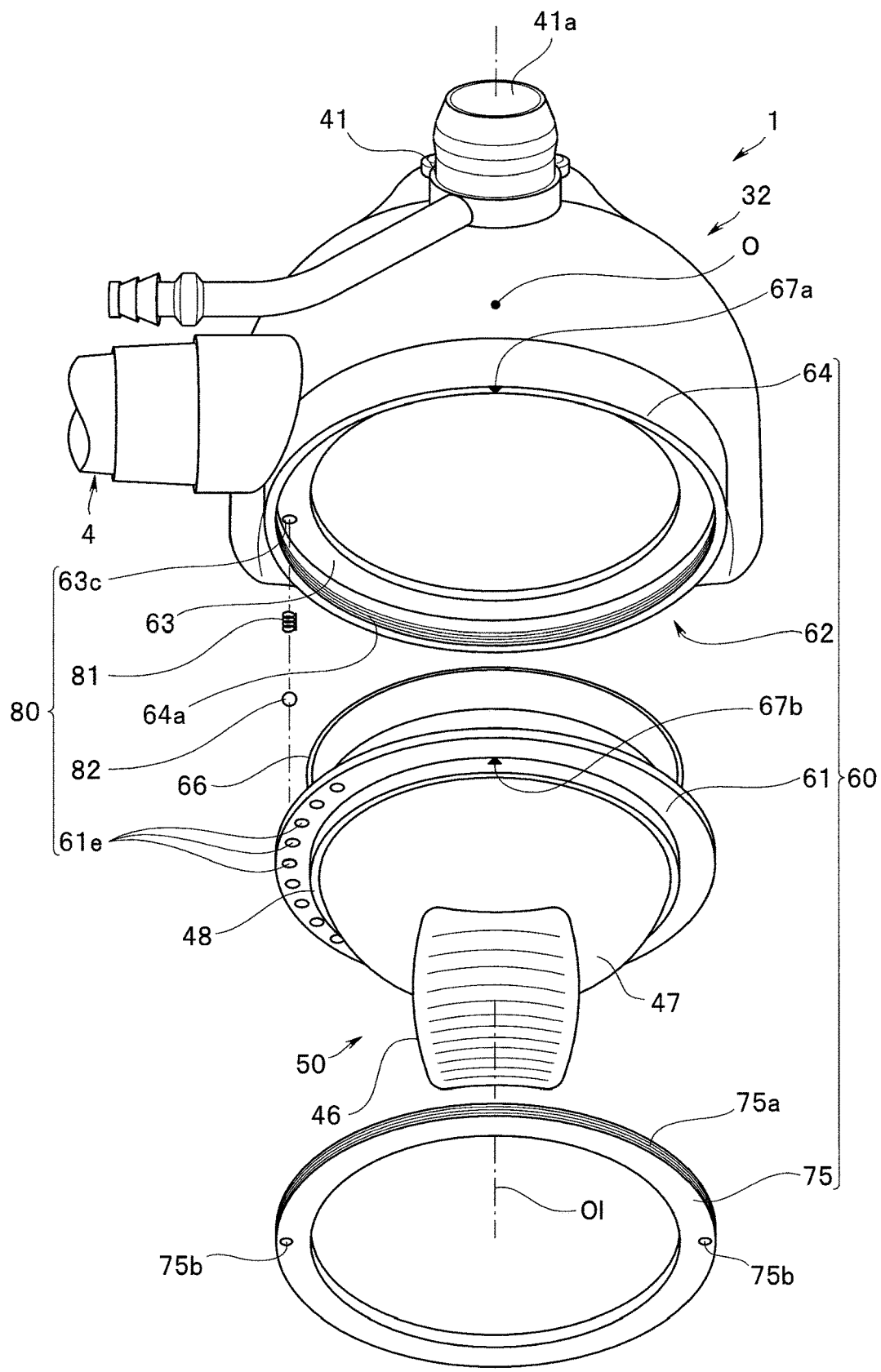
FIG. 20 is an exploded perspective view illustrating a variable fixation mechanism configured between an operation portion main body and a bending operation mechanism according to a fifth modification.
Figure 21:
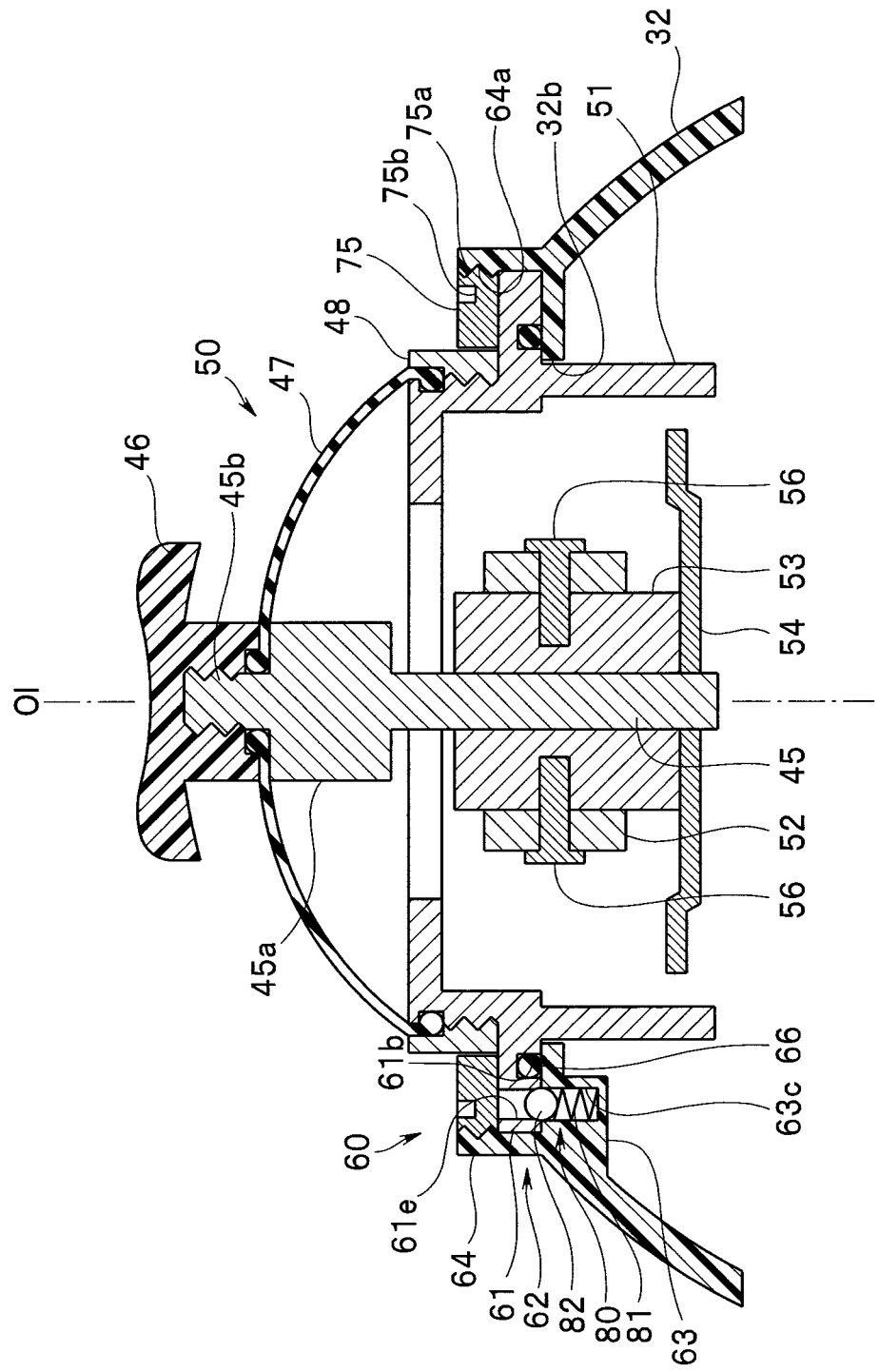
FIG. 21 is a sectional view illustrating a major portion of each of the bending operation mechanism and the variable fixation mechanism according to the fifth modification.

For example, as illustrated in FIGS. 20 and 21, the variable fixation mechanism 60 having a configuration in which the pressing member 75 formed of an annular plate is assembled on the wall portion 64 of the flange accommodation chamber 62 and the outward flange 61 is nipped between the pressing member 75 and the inward flange 63 can be provided with a click stop mechanism 80 that can rotate the bending operation mechanism 50 with respect to the operation portion main body 32 at a predetermined angle step of, for example, about one to five degrees.

Specifically, in the present modification, the inner diameter of the wall portion 64 that configures the flange accommodation chamber 62 is set to a value that is substantially the same as the outer diameter of the outward flange 61.

The internal thread portion 64*a* is provided on the inner periphery of the wall portion 64.

The external thread portion 75*a* configured to be screwed into the internal thread portion 64*a* is provided on the outer periphery of the pressing member 75.

In the variable fixation mechanism 60 configured as described above, the external thread portion 75*a* of the pressing member 75 is screwed into the internal thread portion 64*a* of the wall portion 64 and the outward flange 61 is nipped between the pressing member 75 and the inward flange 63, so that the bending operation mechanism 50 is held rotatably about the central axis OI.

The inward flange 63 is provided with spring accommodation holes 63*c*, and a spring 81 is accommodated in the spring accommodation hole 63*c*.

In the outward flange 61, a plurality of ball receiving holes 61*e* are arranged in an arc shape about the central axis OI at positions respectively corresponding to the spring accommodation holes 63*c*. A ball 82 that is urged against the spring 81 is pressed against any one of the ball receiving holes 61*e*, thereby fixing the rotation position about the central axis OI of the bending operation mechanism 50.

In this configuration, when the user or the like provides a predetermined torque or more about the central axis OI to the bending operation mechanism 50, the ball 82 is pushed out from the ball receiving holes 61*e* against an urging force of the spring 81, thereby allowing the rotation of the bending operation mechanism 50. Along with the rotation, the ball 82 is pressed against another ball receiving hole 61*e* that is adjacent to the previously-pressed ball receiving hole 61*e*, thereby prohibiting the rotation of the bending operation mechanism 50 again and fixing the bending operation mechanism to a new rotation position.

According to the modification as described above, the bending operation mechanism 50 can be easily displaced.

In addition, the amount of rotation from the reference position can be checked based on the number of click feelings generated by the click stop mechanism, thereby facilitating restoration to the reference position from the rotated state. Further, since the amount of rotation is set stepwise, the advantageous effect of easily recognizing the rotation position suitable for each user can also be obtained.

Figure 22:
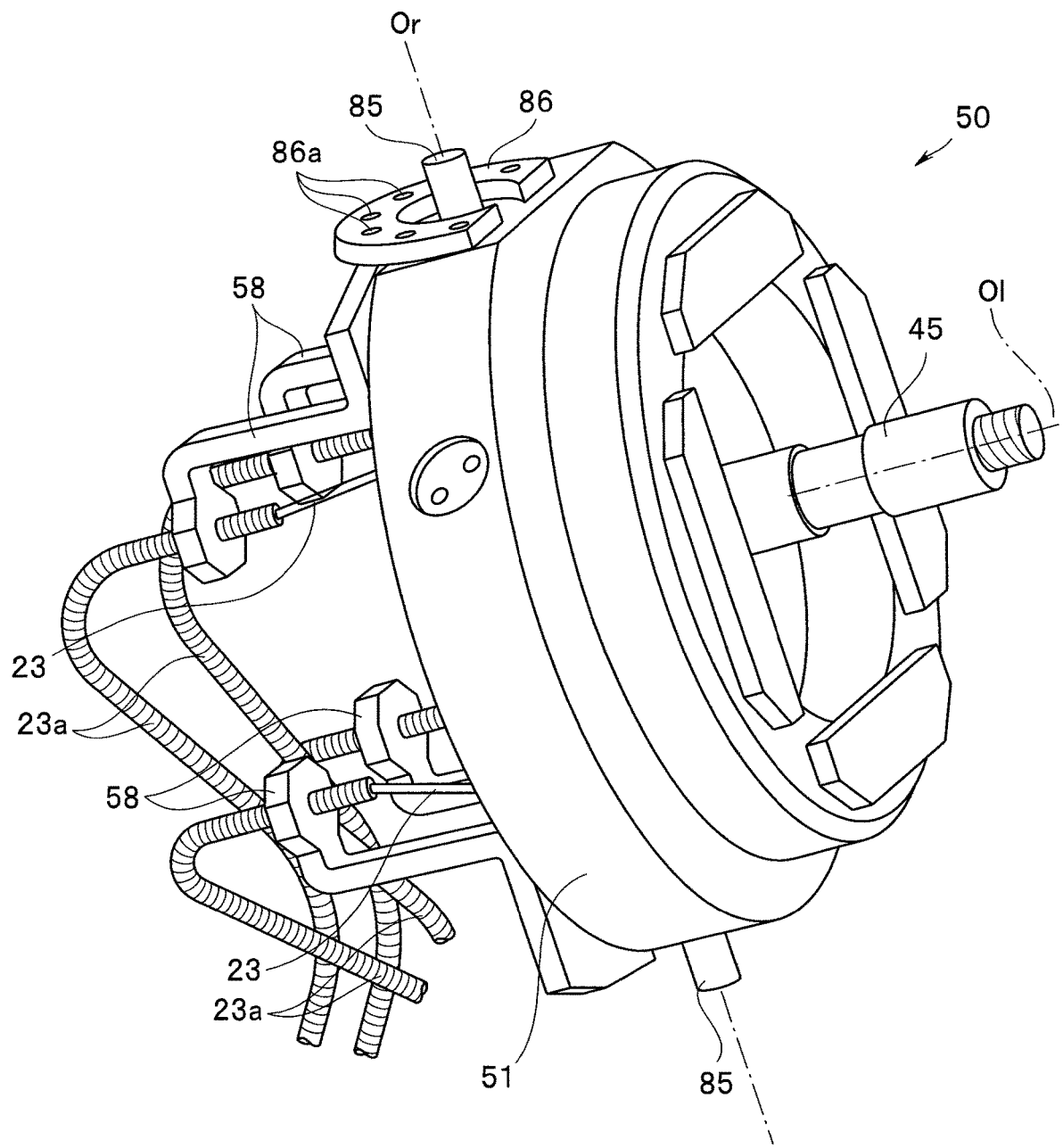
FIG. 22 is a perspective view illustrating a bending operation mechanism according to a sixth modification.
Figure 23:
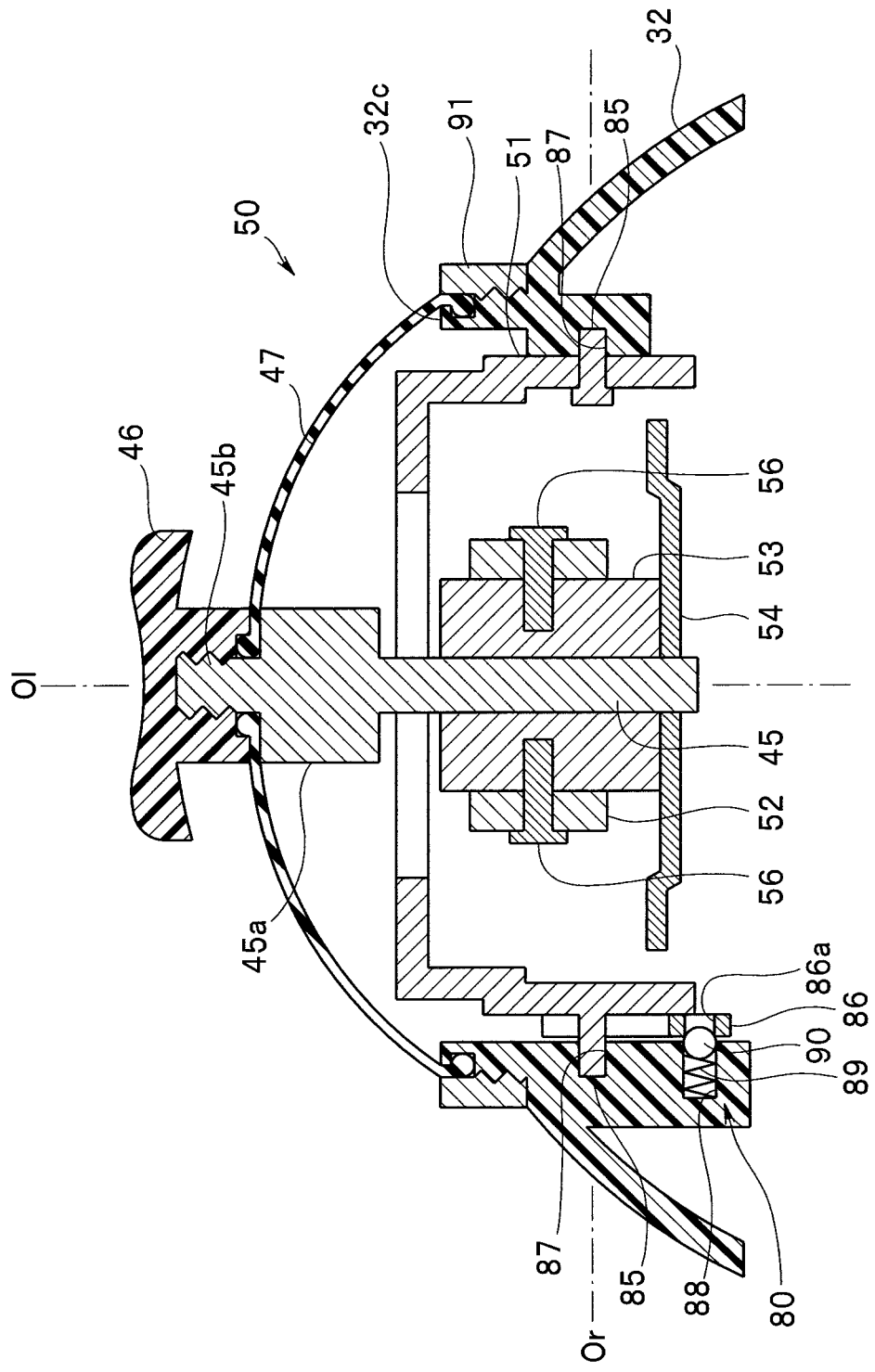
FIG. 23 is a sectional view illustrating a major portion of each of the bending operation mechanism and a variable fixation mechanism according to the sixth modification.

Alternatively, for example, as illustrated in FIGS. 22 and 23, a configuration in which the bending operation mechanism 50 is rotated about a rotation axis Or, which is set in the direction intersecting the central axis OI, can be adopted as the variable fixation mechanism 60.

Specifically, in the present modification, the housing 51 of the bending operation mechanism 50 is provided with a pair of rotation axis portions 85 that extends along the rotation axis Or perpendicular to the central axis OI at a position that is rotationally symmetrical to the central axis OI.

The housing 51 is provided with a ball receiving plate 86 that is formed in a partially arc shape concentrically with the rotation axis portions 85. On the ball receiving plate 86, a plurality of ball receiving holes 86a are arranged in an arc shape about the rotation axis Or.

The operation portion main body 32 is provided with bearing holes 87 corresponding to the rotation axis portions 85. Further, the operation portion main body 32 is provided with a spring accommodation hole 88 at a position corresponding to the arc along which the ball receiving holes 86a are arranged. A spring 89 is accommodated in the spring accommodation hole 88.

Further, a ball 90 that is urged against the spring 89 is pressed against any one of the ball receiving holes 86a, thereby fixing the rotation position about the rotation axis Or of the bending operation mechanism 50.

In the configuration as described above, when a predetermined torque or more about the rotation axis Or is provided to the bending operation mechanism 50 by the user or the like, the ball 90 is pushed out from the ball receiving holes 86a against an urging force of the spring 89, thereby allowing the rotation of the bending operation mechanism 50. Along with the rotation, the ball 90 is pressed against another ball receiving hole 86a that is adjacent to the previously-pressed ball receiving hole 86a, thereby prohibiting the rotation of the bending operation mechanism 50 again and fixing the bending operation mechanism to a new rotation position.

In the present modification in which the bending operation mechanism 50 is displaced by the rotation about the rotation axis Or as described above, a stopper ring 91 is screwed into the outer periphery of the wall portion 32c projecting from the operation portion main body 32 and the other end side of the external cover 47 is nipped between the wall portion 32c and the stopper ring 91, thereby being connected to the operation portion main body 32 in a liquid-tight state.

Note that the present invention is not limited to the above-described embodiments and various modifications and changes can be made. Such modifications and changes are also included in the technical scope of the present invention. For example, the configurations according to the above-described embodiments and the configurations according to the modifications may be combined as appropriate.

What is claimed is:

1. An operation portion for use with an endoscope, the operation portion comprising:
    an operation portion body;
    a bending operation mechanism rotatably disposed in the operation portion body to rotate relative to the operation portion body between a first rotational position and a second rotational position, the bending operation mechanism including a lever configured to be tilted in at least one predetermined operation direction to cause a bending portion provided in an insertion portion configured to be inserted into a subject to be bent in a corresponding predetermined bending direction;
    wherein the bending operation mechanism is rotatably disposed in the operation portion body such that the at least one predetermined operation direction of the lever rotates relative to the operation portion body when the bending operation mechanism rotates from the first rotational position to the second rotational position.

2. The operation portion according to claim 1, wherein the bending operation mechanism is configured to rotate about a central axis of the lever located at a neutral position.

3. The operation portion according to claim 1, wherein:
    the operation portion body having one of a protrusion and a hole;
    the bending operation mechanism having an other of the protrusion and the hole; and
    the protrusion is disposed in the hole and the hole is formed in an arc shape having a center on a central axis of the lever.

4. The operation portion according to claim 3, wherein the protrusion is one of a threaded stud or thread screw disposed in a mating threaded hole in one of the operation portion body or the bending operation mechanism.

5. The operation portion according to claim 1, further comprising a click stop mechanism configured to rotate the bending operation mechanism in a predetermined angle with respect to the operation portion body, the click stop mechanism being provided between the bending operation mechanism and the operation portion body.

6. The operation portion according to claim 1, wherein:
    the bending operation mechanism has a first flange;
    the operation portion body has a pocket and a second flange sandwiching the first flange;
    the first flange of the bending operation mechanism rotatably sliding relative to the second flange and the pocket about a central axis of the lever located at a neutral position.

7. The operation portion according to claim 6, further comprising:
    a click stop mechanism configured to rotate the bending operation mechanism in a predetermined angle with respect to the operation portion body, the click stop mechanism being provided between the bending operation mechanism and the operation portion body.

8. The operation portion according to claim 1, wherein:
    the bending operation mechanism has a flange, the flange having a first position rotatably fixed to the operation portion body, the flange having a second position slidingly fixed to the operation portion body; and
    the bending operation mechanism rotates about the first position and slides with respect to the operation portion body at the second position.

9. The operation portion according to claim 1, wherein an index indicating a neutral position of the bending operation mechanism is displayed on the operation portion body and on the bending operation mechanism.

10. An endoscope comprising:
    the operation portion according to claim 1;
    the insertion portion configured to be inserted into the subject and to be bent in directions including, up, down, left, and right directions; and
    the operation portion provided at a proximal end side of the insertion portion, the operation portion being provided with a grasping portion configured to be grasped by an operator.

11. The operation portion according to claim 1, wherein the operation portion body comprises:
    an engagement portion configured to be engaged with a hole provided at one of the bending operation mechanism and the operation portion body, and
    the engagement portion is disposed in the hole and the bending operation mechanism is supported such that the bending operation mechanism is rotatable relative to the operation portion.

12. The operation portion according to claim 11, wherein the engagement portion comprises a pin.

13. The operation portion according to claim 12, wherein the pin extends along a central axis of the lever located at a neutral position.

14. The operation portion according to claim 11, wherein the engagement portion is provided in an other of the bending operation mechanism and the operation portion body.

15. The operation portion according to claim 11, wherein the hole has an arc shape having a center on a central axis of the lever located at a neutral position.

16. The operation portion according to claim 11, wherein the hole is provided along a circumferential direction of a central axis of the lever located at a neutral position.

17. The operation portion according to claim 1, wherein the lever is configured to be tilted relative to a central axis of the lever located at a neutral position, the central axis is maintained in the first rotational position and the second rotational position.

18. The operation portion according to claim 1, further comprising:
at least one wire configured to bend the bending portion; and
at least one stay configured to apply tension to the at least one wire.

19. The operation portion according to claim 1, wherein the bending operation mechanism comprises an index on an outer surface to indicate a neutral position of the bending operation mechanism.

20. The operation portion according to claim 1, wherein:
the operation portion body having one of first and second protrusions and first and second holes;
the bending operation mechanism having an other of the first and second protrusions and the first and second holes; and
the first and second protrusions are disposed in the first and second holes, respectively, and the first and second holes are each formed in an arc shape having a center on a central axis of the lever.

\* \* \* \* \*